United States Patent
Bell, III et al.

(10) Patent No.: US 9,814,790 B2
(45) Date of Patent: *Nov. 14, 2017

(54) EUKARYOTIC CELLS WITH ARTIFICIAL ENDOSYMBIONTS FOR MULTIMODAL DETECTION

(71) Applicant: Bell Biosystems, Inc., Palo Alto, CA (US)

(72) Inventors: Caleb B. Bell, III, San Mateo, CA (US); Alexey Bazarov, Fremont, CA (US)

(73) Assignee: Bell Biosystems, Inc., Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/594,594

(22) Filed: May 13, 2017

(65) Prior Publication Data

US 2017/0246325 A1    Aug. 31, 2017

Related U.S. Application Data

(63) Continuation of application No. 15/263,144, filed on Sep. 12, 2016, now Pat. No. 9,657,358, which is a continuation of application No. 15/079,453, filed on Mar. 24, 2016, now Pat. No. 9,446,154, which is a continuation of application No. 14/689,987, filed on Apr. 17, 2015, now Pat. No. 9,315,780, which is a continuation of application No. 14/332,373, filed on Jul. 15, 2014, now Pat. No. 9,023,612, which is a continuation-in-part of application No. 13/838,717, filed on Mar. 15, 2013, now Pat. No. 8,828,681, which is a continuation-in-part of application No. 13/374,799, filed on Jan. 13, 2012, now Pat. No. 8,956,873, and a continuation-in-part of application No. PCT/US2013/021414, filed on Jan. 14, 2013, which is a continuation-in-part of application No. 13/374,799, filed on Jan. 13, 2012, now Pat. No. 8,956,873.

(51) Int. Cl.
    *C12N 1/20*    (2006.01)
    *A61K 49/00*   (2006.01)
    *G01N 33/50*   (2006.01)
    *A61K 51/12*   (2006.01)

(52) U.S. Cl.
    CPC ...... *A61K 49/0097* (2013.01); *A61K 51/1203* (2013.01); *G01N 33/5091* (2013.01)

(58) Field of Classification Search
    None
    See application file for complete search history.

(56) References Cited

U.S. PATENT DOCUMENTS

| | | |
|---|---|---|
| 4,385,119 A | 5/1983 | Blakemore |
| 4,677,067 A | 6/1987 | Schwartz et al. |
| 5,843,643 A | 12/1998 | Ratner et al. |
| 6,004,815 A | 12/1999 | Portnoy et al. |
| 6,287,556 B1 | 9/2001 | Portnoy et al. |
| 6,436,694 B1 | 8/2002 | Tally et al. |
| 6,599,502 B2 | 7/2003 | Portnoy et al. |
| 7,390,646 B2 | 6/2008 | Andino-Pavlovsky et al. |
| 7,470,427 B2 | 12/2008 | Cocking |
| 7,754,221 B2 | 7/2010 | Szalay et al. |
| 8,021,662 B2 | 9/2011 | Szalay et al. |
| 8,159,224 B2 | 4/2012 | Fontius |
| 8,361,437 B2 | 1/2013 | Sharma et al. |
| 8,406,498 B2 | 3/2013 | Ortyn et al. |
| 8,828,681 B2 * | 9/2014 | Bell, III ............ A61K 49/1896 424/9.34 |
| 8,859,281 B2 | 10/2014 | Bell, III et al. |
| 8,956,873 B2 * | 2/2015 | Bell, III ............ C12N 5/00 435/252.3 |
| 9,023,612 B2 * | 5/2015 | Bell, III ............ A61K 49/0097 435/29 |
| 9,370,566 B2 * | 6/2016 | Bell, III ............ C12N 15/03 |

(Continued)

FOREIGN PATENT DOCUMENTS

| EP | 1807517 B1 | 10/2011 |
|---|---|---|
| WO | WO 2010/109187 | 9/2010 |

(Continued)

OTHER PUBLICATIONS

Gage et al., Use of green fluorescent protein to visualize the early events of symbiosis between Rhizobium meliloti and alfalfa, 1996, J. Bacteriol. vol. 178, pp. 7159-7166.

Goetz et al., Microinjection and growth of bacteria in the cytosol of mammalian host cells, 2001, Proc. Natl Acad. Sci. vol. 98, pp. 12221-12226.

Linhartova et al., RTX proteins: a hihgly diverse family secreted by a common mechanism, 2010, FEMS Microbiol. Rev. vol. 34, pp. 1076-1112.

Bian et al., The endosymbiotic bacterium Wolbachia induces resistance to dengue virus in Aedes aegypti, PLos Pathogen vol. 6, p. e1000833 (2010).

Calvitti, Bacteria endosymbionts: a source of innovation in biotechnology for the control of vector borne diseases, Energia Amb. Innovaz. n. 6, Nov.-Div 2011, pp. 49-57.

Linhartova et al., RTX proteins: a highly diverse family secreted by a common mechanism, 2010, FEMS Microbiol. Rev. vol. 34, pp. 1076-1112.

(Continued)

*Primary Examiner* — Jim Ketter
(74) *Attorney, Agent, or Firm* — HelixIP

(57) ABSTRACT

The present invention is directed generally to eukaryotic cells comprising single-celled organisms that are introduced into the eukaryotic cell through human intervention and which transfer to daughter cells of the eukaryotic cell, and methods of introducing such single-celled organisms into eukaryotic cells. The invention provides single-celled organisms that introduce a phenotype to eukaryotic cells that is maintained in daughter cells. The invention additionally provides eukaryotic cells containing magnetic bacteria. The invention further provides eukaryotic cells engineered with single-celled organisms to allow for multimodal observation of the eukaryotic cells. Each imaging method (or modality) allows the visualization of different aspects of anatomy and physiology, and combining these allows the imager to learn more about the subject being imaged.

20 Claims, 9 Drawing Sheets

(56) References Cited

U.S. PATENT DOCUMENTS

| | | | |
|---|---|---|---|
| 9,446,154 B2* | 9/2016 | Bell, III | A61K 49/0097 |
| 9,528,980 B2* | 12/2016 | Bell, III | A61K 49/1896 |
| 2002/0012698 A1 | 1/2002 | Bauerlein et al. | |
| 2004/0234455 A1 | 11/2004 | Szalay | |
| 2005/0069491 A1 | 3/2005 | Szalay et al. | |
| 2007/0202572 A1 | 8/2007 | Szalay et al. | |
| 2007/0258886 A1 | 11/2007 | Ahrens et al. | |
| 2007/0275924 A1 | 11/2007 | Khan | |
| 2009/0181101 A1 | 7/2009 | Rademacher et al. | |
| 2009/0311194 A1 | 12/2009 | Hu et al. | |
| 2009/0325258 A1 | 12/2009 | Matsunaga et al. | |
| 2010/0135912 A1 | 6/2010 | Gambhir | |
| 2010/0297022 A1 | 11/2010 | Prato et al. | |
| 2011/0034753 A1 | 2/2011 | Dobson et al. | |
| 2012/0021517 A1 | 1/2012 | Jin et al. | |
| 2012/0184004 A1 | 7/2012 | Kay et al. | |
| 2012/0184030 A1 | 7/2012 | Dermanovic et al. | |
| 2012/0302819 A1 | 11/2012 | Alphandery et al. | |
| 2013/0183758 A1 | 7/2013 | Bell, III et al. | |
| 2013/0224122 A1 | 8/2013 | Gambhir et al. | |
| 2013/0253303 A1 | 9/2013 | Bell, III et al. | |
| 2013/0280173 A1 | 10/2013 | Negev et al. | |
| 2014/0273203 A1 | 9/2014 | Bell, III et al. | |
| 2015/0007359 A1 | 1/2015 | Bell, III et al. | |
| 2015/0010937 A1 | 1/2015 | Bell, III et al. | |
| 2015/0064787 A1 | 3/2015 | Bell, III et al. | |

FOREIGN PATENT DOCUMENTS

| | | |
|---|---|---|
| WO | WO 2010/111409 | 9/2010 |
| WO | WO 2011/007110 | 1/2011 |
| WO | WO 2013/106814 | 7/2013 |
| WO | WO 2013106814 | 7/2013 |
| WO | WO 2014/039768 | 3/2014 |
| WO | WO 2014145785 | 9/2014 |
| WO | WO 2015034962 | 3/2015 |

OTHER PUBLICATIONS

Yan et al, Magnetotactic bacteria, magnetosomes and their application, Microbial. Res. (May 9, 2012) vol. 167, pp. 507-519.

Re U.S. Appl. No. 90/008,857, filed Oct. 7, 2008, Portnoy, Daniel A. et al.

Re U.S. Appl. No. 90/008,859, filed Sep. 30, 2008, Portnoy, Daniel A. et al.

Re U.S. Appl. No. 90/008,860, filed Oct. 14, 2008, Portnoy, Daniel A. et al.

Agapakis, C.M. et al., Towards a synthetic chloroplast, PLoS ONE, Apr. 2011, 6: e18877.

Ben-Haim, N. et al., Cell-specific integration of artificial organelles based on functionalized polymer vesicles, Nano Lett., 2008, 8:1368-1373.

Benoit, M.R. et al., Visualizing implanted tumors in mice with magnetic resonance imaging using magnetotactic bacteria, Clin. Canc. Res., Aug. 15, 2009, 15(16):5170-5177.

Benoit, M.R. et al., Supp. Figs., Clin. Canc. Res., 2009, at: http://clincancerres.aacrjournals.org/content/suppl/2009/08/11/1078-0432.CCR-08- 3206.DC1/Suppiementary_Data.pdf.

Bernsen, M.R. et al., Labelling of mammalian cells for visualisation by MRI, Eur. Radial., 2010, 20: 255-274.

Bhattacharya, D. et al., Photosynthetic eukaryotes unite: endosymbiosis connects the dots, BioEssays, 2003, 26:50-60.

Bielecki, J. et al., Bacillus subtilis expressing a haemolysin gene from Listeria monocytogenes can grow in mammalian cells, Nature, May 10, 1990, 345:175-176.

Bitterman, P.B. et al., Alveolar macrophage replication, J. Clin. Inv., Aug. 1984, 74: 460-469.

Blakemore, R., Magnetotactic bacteria, Science, Oct. 24, 1975, 190(4212): 377-379.

Blakemore, R.P. et al., Isolation and pure culture of a freshwater magnetic spirillum in chemically defined medium, J. Bacteriol. Nov. 1979, 140(2): 720-729.

Bonnett, H.T., On the mechanism of the uptake of Vaucheria chloroplasts by carrot protoplasts treated with polyethylene glycol, Planta, 1976, 131: 229-233.

Brown, M.B. et al., Exploiting tumour hypoxia in cancer treatment, Nat. Rev. Cancer, Jun. 2004, 4: 437-447.

Budde, M.B. et al., Magnetic tagging of therapeutic cells for MRI, J. Nucl. Med., Feb. 2009, 50(2): 171-174.

Bulte, J.W.M., In vivo MRI cell tracking: clinical studies, AJR Am. J. Roentgenol., Aug. 2009, 193(2): 314-325.

Burdette, D.L. et al., Vibrio VopQ induces PI3-kinase-independent autophagy and antagonizes phagocytosis, Mol. Microbiol., 2009, 73(4): 639-649.

Burgess, J.G. et al., Evolutionary relationships among Magnetospirillum strains inferred from phylogenetic analysis of 16S rDNA sequences, J. Bacterioi, 1993, 175: 6689-6694.

Camilli, A. et al., Listeria monocytogenes mutants lacking phosphatidylinositol-specific phospholipase C are avirulent, J. Exp. Med., Mar. 1991, 173: 751-754.

Cao, F. et al., In vivo visualization of embryonic stem cell survival, proliferation, and migration after cardiac delivery, Circulation, 2006, 113:1005-1014.

Cheng, K. et al., Magnetic enhancement of cell retention, engraftment, and functional benefit . . . , Cell Transplant., 2012, 21: 1121-1135.

Chico-Calero, I. et al., Hpt, a bacterial homolog of the microsomal glucose-6-phosphate translocase . . . , Proc. Natl Acad. Sci., Jan. 8, 2002, 99(1): 431-436.

Chomel, B.B. et al., Ecological fitness and strategies of adaptation of *Bartonella* species to their hosts and vectors, Vet. Res., 2009, 40: 29.

Cocking, E.C., et al., Symbiosome-like intracellular colonization of cereals and other crop plants by nitrogen-fixing bacteria . . . , Chin. Acad. Sci., 2005, 48: 888-896.

Cocking, E.C., et al., Intracellular colonization of roots of arabidopsis and crop plants by Gluconacetobacter diazotrophicus, In Vitro. Cell. Dev. Biol., 2006, 42: 74-82.

Concord, C. et al., Long-term evolutionary stability of bacterial endosymbiosis in Curculionoidea . . . , Mol. Biol. Evol., 2008, 25(5): 859-868.

Corchero, J.L. et al., Biomedical applications of distally controlled magnetic nanoparticles, Trends Biotechnol., 2009, 27(8): 468-476.

Dale, C. et al., The insect endosymbiont Sodalis glossinidius utilizes a type III secretion system for cell invastion, Proc. Natl Acad. Sci., Feb. 13, 2001, 98(4): 1883-1888.

Dang, L.H., et al., Combination bacteriolytic therapy for the treatment of experiemental tumors, Proc. Natl Acad. Sci., Dec. 18, 2001, 98(26): 15155-15160.

Dubreuil, R. et al., Bringing host-cell takeover by pathogenic bacteria to center stage, Cell. Logist., 2011, 1(4): 120-124.

Dyall, S.D. et al., Ancient invasions: from endosymbionts to organelles, Science, 2004, 304: 253-257.

Faivre, D. et al., Magnetotactic bacteria and magnetosomes, Chem. Rev. 2008, 108: 4875-4898.

Felfoul, O. et al., Mr imaging of Fe—Co nanoparticles, magnetotactic bacteria . . . , Proc. of the 7th IEEE International. Conf. on Nanotech., 2008, pp. 308-301.

Finlay, B.B. et al., Common themes in microbial pathogenicity revisited, Microbiol. Mol. Biol. Rev., Jun. 1997, 61(2): 136-169.

Fritsche, T.R. et al., Phylogenetic diversity among geographically dispersed Chlamydiales endosymbionts . . . , Appl. Environ. Microbiol., Jun. 2000, 66(6): 2613-2619.

Goebel, W. et al., Intracellular survival strategies of mutualistic and parasitic prokaryotes, Trends Microbiol., Jun. 2001, 9(6): 267-273.

Goetz, M. et al., Microinjection and growth of bacteria in the cytosol of mammalian host cells, Proc. Natl Acad. Sci., Oct. 9, 2001, 98(21): 12221-12226.

Gordon, S. et al., Monocyte and macrophage heterogeneity, Nat. Rev., Dec. 2005, 5: 953-964.

Gupta, R.S. et al., Phylogenomics and signature proteins for the alpha Proteobacteria and its main groups, BMC Microbiol., Nov. 28, 2007, 7:106.

(56) References Cited

OTHER PUBLICATIONS

Hackam, D.J. et al. Rho is required for the initiation of Calcium signaling and phagocytosis by Fcy receptors in macrophages, J. Exp. Med., Sep. 15, 1997, 186(6): 955-966.
Hacker, H. et al., Caspase-9/-3 activation and apoptosis are induced in mouse macrophage upon ingestion and digestion of *E. coli* bacteria, J. Immunol., 2002, 169: 3172-3179.
Hayward, R.D. et al., Direct nucleation and bundling of actin by the SipC protein of invasive Salmonella, EMBO J., 1999, 18(18): 4926-4934.
Himmerlreich, U. et al., Stem cell labeling for magnetic resonance imaging, Min. Inv. Ther., 2008, 17:132-142.
Hong, P.C. et al., Identification of genes required for chronic persistence of *Brucella abortus* in mice, Infect. Immun., Jul. 2000, 68(7): 4102-4107.
Huang, J. et al., Phylogenomic evidence supports past endosymbiosis, intracellular and horizontal gene transfer in Cryptosporidium parvum, Genome Biol., Oct. 19, 2004, 5:R88.
Joseph, B. et al., Identification of Listeria monocytogenes contributing to intracellular replication by expression profiling . . . , J. Bacterial., Jan. 2006, 188(2): 556-68.
Judas, M. et al., Genomic islands tools of bacterial horizontal gene transfer and evolution, FEMS Microbiol. Rev., 2009, 33: 376-393.
Jutila, M.A. et al., Locally dividing macrophages in normal and inflamed mammary glands, Clin. Exp. Immunol., 1986, 66: 615-624.
Kasinaskas, R.W. et al., Salmonella typhimurium lacking ribose chemoreceptors localize in tumor quience and induce apoptosis, Cancer Res., 2007, 67(7): 3201-3209.
Kawaguchi, R. et al., Phylogeny and 16s rRNA sequence of *Magnetospirillum* sp. AMB-1, an aerobic magnetic bacterium, Nucleic Acids, Res., 1992, 20(5): 1140.
Kimura, N.T. et al., Selective localization and growth of Bifidobacterium bifidum in mouse tumors following intravenous administration, Cancer Res., Jun. 1980, 40: 2061-2068.
Kircher, M.F. et al., Noninvasive cell-tracking methods, Nat. Rev. Clin. Oncol., 2011, 8:677-688.
Kraitchman, D.L. et al., Imaging of stem cells using MRI, Basic Res. Cardiol., 2008, 103: 105-113.
Kraitchman, D.L. et al., Stem cell therapy: MRI guidance and monitoring, 2008, J. Magn. Reson. Imaging 27: 299-310.
Lane, C.E. et al., The eukaryotic tree of life: endosymbiosis takes its TOL, Trends Ecol. Evol., 2008, 23(5): 268-275.
Lang, C. et al., Expression of green fluorescent protein fused to magnetosome proteins in microaerophilic magnetotactic bacteria, Appl. Environ. Microbiol., 2008, 74: 4944-53.
Lee, Z. et al., Imaging stem cell implant for cellular-based therapies, Exp. Biol. Med., 2008, 233: 930-940.
Lemmon, M.J. et al., Anaerobic bacteria as a gene delivery system that is controlled by the tumor microenvironment, Gene Ther., 1997, 4: 791-796.
Li, L.H. et al., Electrofusion between heterogeneous-sized mammalian cells in a pellet: potential applications in drug delivery . . . , Biophysical J., Jul. 1996, 71: 479-486.
Liu, S. et al., Anticancer efficacy of systemically delivered anaerobic bacteria as gene therapy vectors targeting tumor hypoxia/necrosis, Gene Ther., 2002, 9: 291-296.
Loessner, H. et al., Remote control of tumour-targeted *Salmonella entrerica* serovar Typhimurium by the use of L-arabinose . . . , Cell. Microbiol., 2007, 9(6): 1529-1537.
Login, F.H. et al., Antimicrobial peptides keep insect endosymbionts under control, Science, Oct. 21, 2011, 334: 362-365.
Long, C.M. et al., In vivo tracking of cellular therapeutics using magnetic resonance imaging, Expert Opin. Biol. Ther., 2009, 9(3): 293-306.
Long, M.E. et al., Disruption of Francisella tularensis schu S4 igll, iglJ, and pdpC genes results in attenuation . . . , Infect. Immun., Mar. 2013, 81(3): 850-861.

Martel, S. et al., Towards MRI-controlled ferromagnetic and MC-1 magnetotactic bacterial carriers . . . , Proceed. 28th IEEE EMBS Ann. Intl Conf. NY, 2006, pp. 3399-3402.
Matsunaga, T. et al., Phagocytosis of bacterial magnetite by leucocytes, Appl. Microbiol. Biotechnol., 1989, 31:401-405.
Matsunaga, T. et al., Gene transfer in magnetic bacteria: transposon mutagenesis and cloning of genomic DNA fragments . . . , J. Bacterial., May 1992, pp. 2748-2753.
Matsunaga, T. et al., Complete genome sequence of the facultative anaerobic magnetotactic bacterium *Magnetospirillum* sp. strain AMB-1, DNA Res., 2005, 12: 157-166.
Matsunaga, T. et al., Molecular bioengineering of bacterial magnetic particles . . . , Magnetoreception and Magnetosomes in Bacteria, 2006, pp. 227-254, Springer-Verlag, Berlin.
Min, J. et al., Quantitative bioluminescence imaging of tumor-targeting bacteria in living animals, Nat. Protocols, 2008, 3(4): 629-636.
Nishida, K. et al., Induction of biogenic magnetization and redox control by a component of the target of rapamycin complex 1 signaling pathway, PLoS Biol., 2012, 10:e1001269.
Okamoto, N. et al., A secondary symbiosis in progress?, Science, Oct. 14, 2005, 310: 287.
Oldroyd. G.E.D. et al., Reprogramming plant cells for endosymbiosis, Science, May 8, 2009, 324: 753-754.
O'Riordan, M. et al., Innate recognition of bacteria by a macrophage cytosolic surveillance pathway, Proc. Natl Acad. Sci., Oct. 15, 2002, 99(21): 13861-13866.
Pan, X. et al., Cationic lipid-coated magnetic nanoparticles associated with transferrin for gene delivery, Int. J. Pharm., Jun. 24, 2008, 358: 263-70.
Pawelek, J.M. et al., Tumor-targeted *Salmonella* as a novel anti-cancer vector, Cancer Res., Oct. 15, 1997, 57: 4537-4544.
Price, C.T.D. et al., Amoeba host-Legionella synchronization of amino acid auxotrophy and its role in bacterial adaptation . . . , Environ. Microbiol., 2013, 16(2): 350-358.
QIU, B. et al., Dual transfer of GFP gene and MGd into stem-progenitor cells, Acad. Radiol., 2010, 17: 547-552.
Riegler, J. et al., Superparamagnetic iron oxide nanoparticle targeting of MSCs in vascular injury, Biomaterials, 2013, 34: 1987-1994.
Rogers, W.J. et al., Technology insight: in vivo cell tracking by use of MRI, Nature Clin. Prac., Oct. 2006, 3(10): 554-562.
Roodbeen R. et al., Synthetic cells and organelles: compartmentalization strategies, BioEssays, 2009, 31: 1299-1308.
Salminen, M. et al., Improvement in nuclear entry and transgene expression of baculoviruses by disintegration of microtubules . . . , J. Virol., Mar. 2005, 79(5): 2720-2728.
Schaffer, D. et al., Biological imaging in animals with genetically encoded magnetic reporters, Jan. 30, 2013, at http://www.berkeley.edu/news2/2013/01/KeckAbstract.htm.
Scheffel, A. et al., The acidic repetitive domain of the Magnetospirillum gryphiswaldense MamJ protein . . . , J. Bacteriol., Sep. 2007, 189(17): 6437-6446.
Schoen, P. et al., Gene transfer mediated by fusion protein hemagglutinin reconstituted in cationic lipid vesicles, Gene Ther., 1999, 6:823-832.
Schuler, D. et al., Dynamics of iron uptake and Fe3O4 biomineralization during aerobic and microaerobic growth . . . , J. Bacteriol., 1998, 180(1): 159-162.
Schuler, D. et al., Bacterial magnetosomes: microbiology, biomineralization, and biotechnological applications, Appl. Microbiol. Biotechnol., 1999, 52: 464-473.
Schultheiss, D. et al., Inactivation of the flagellin gene flaA in Magnetospirillum gryphiswaldense . . . , Appl. Environ. Microbiol., Jun. 2004, 70(6): 3624-2631.
Shoemaker, R.H., The NCI60 human tumour cell line anticancer drug screen, Nature Rev., Oct. 2006, 6: 813-823.
Silva, A.C. et al., Application of hyperthermia induced by superparamagnetic iron oxide nanoparticles in glioma treatment, Intl J. Nanomed., 2011, 6:591-603.
Smith, G.A. et al., The two distinct phospholipases C of Listeria monocytogenes have overlapping roles . . . , Infect. Immun., Nov. 1995, 63(11): 4231-4237.

(56) References Cited

OTHER PUBLICATIONS

Soghomonyan, S.A. et al., Positronic emissions tomography (PET) imaging of tumor-localized Salmonella expressing HSV1-TK, Cancer Gene Ther., 2005, 12: 101-108.
Stewart, F.J. et al., Lateral symbionts acquisition in a maternally transmitted chemosynthetic clam endosymbiosis, Mol. Biol. Evol., 2008, 25(4): 673-687.
Sugimoto, Y. et al., Differential cell division history between neutrophils and macrophages, British J. of Haematology, 2006, 135: 725-731.
Swiston, A.J. et al., Surface functionalization of living cells with multilayer patches, Nano Lett., 2008, 8(12): 4446-4453.
Sznol, M. et al., Use of preferentially replicating bacteria for the treatment of cancer, J. Clin. Invest., Apr. 2000, 105(8): 1027-1030.
Thao, M.L. et al., Phylogenetic analysis of vertically transmitted psyllid endosymbionts (*Candidatus Carsonella ruddi*) . . . , Curr. Microbiol., 2001, 42: 419-421.
Vaishnava, S. et al., The cell biology of secondary endosymbiosis—how parasites build, divide and segregate the apicoplast, Mol. Microbiol., 2006, 61(6): 1380-1387.
Valdivia R.H. et al., Endosymbiosis: the evil within, Current Biology, 2007, 17 (11): R408-R410.
Van Der Glezen, M., Endosymbiosis: past and present, Heredity, 2005, 95: 335-336.
Van Furth, R. et al., Dual origin of mouse spleen macrophages, J. Exp. Med., Nov. 1984, 160: 1273-1283.
Verhoeven, H.A. et al., Direct cell to cell transfer of organelles by microinjection, Plant Cell Reports, 1992, 10: 613-616.
Wajnberg, E. et al., Electron paramagnetic resonance study of the migratory ant Pachycondyla marginata abdomens, Biophys. J., Feb. 2000, 78: 1018-1023.
Wenergreen, J.J., Endosymbiosis: lessons in conflict resolution, PLoS Biology, Mar. 2004, 2(3): 307-311.
Widermann, A. et al., Yersinia enterocolitica invasin triggers phagocytosis via B1 integrins, CDC42Hs and WASp in macrophages, Cellular Microbiol., 2001, 3(10): 693-702.
Williams, K. et al., Proliferating cellular nuclear antigen expression as a marker of perivascular macrophages . . . , Am. J. Pathol., Aug. 2002, 161(2): 575-585.
Wyss Institute, New "magnetic yeast" could be significant step in harnessing nature's magnetic capabilities, Feb. 28, 2012, at http://wyss.harvard.edu/viewpressrelease/78.
Xi, Z. et al., Characterization of Wolbachia transfection efficiency by using microinjection of embryonic cytoplasm . . . , Appl. Environ. Microbiol., 2005, 71(6): 3199-3204.
Xie, J. et al., Production, modification, and bio-applications of magnetic nanoparticles gestated by Magnetotactic Bacteria, Nano Res., 2009, 2: 261-278.
Yam, C. et al., Monotherapy with a tumor-targeting mutant of S. typhimurium inhibits liver metastasis in a mouse model . . . , J. Surgical Res., 2010, 164: 248-255.
Yoshida, S. et al., Shigella deliver an effector protein to trigger host microtubule destabilization . . . , EMBO J., 2002, 21(12): 2923-2936.
Zhang, X. et al., Artificial innate immune system . . . , Proc. of the 3rd Int'l Conf. on Artificial Immun. Sys. (ICARIS), LNCS 3239, 2004, pp. 302-315.
Zhao, M. et al., Targeted therapy with a Salmonella typhimurium leucine-arginine auxotroph . . . , Cancer Res., Aug. 1, 2006, 66(15): 7647- 7652.
Zhao, M., et al., Monotherapy with a tumor-targeting mutant of Salmonella typhimurium . . . , Proc. Natl. Acad. Sci., Jun. 12, 2007, 104(24): 10170-10174.
Wixon, Featured Organism: Reductive evolution in bacteria Buchnera sp. Rickettsia Prowazekii and . . . (2001) vol. 2, pp. 44-48.
Klasson et al, Horizontal gene transfer between Wolbachia and the mosquito Aedes aegypti, BMC Genomics (2009) vol. 10, pp. 33-42.
Lovieno et al, Detection of baterial endosymbionts in clinical acanthamoeba isolates, (2010) Ophthalmology vol. 117, pp. 445-452.
Ordway et al, Animal models of mycobacteria infection, Current Protocols in Immunology (2011) Chapter 19, p. 19.5.1.
Bazylinski et al, Magnetosome formation in prokaryotes, 2004, Nature Reviews vol. 2, pp. 217-230.
Bell, Tracking cardiac engraftment and viability of MiPSC by MRI, 2014, Abstract for Grant Application, Project No. 1R43EB019239-01.
Brewer, et al., Relaxometry of Bacterially Derived Organelles: A Novel Class of MRI Contrast Agent for Cell Labeling and Tracking, May 2014, Joint Ann Mtg ISMRM-ESMRMB, Italy.
Chen et al, Microwave breast tumor detection and size estimation using contrast-agent-loaded magnetotactic bacteria, 2013, 35th Ann Intl Conf IEEE EMBS Jul. 3, 2013, pp. 5781-5784.
Frederickson et al, Inhibition of endosomal/lysosomal degradation increases the infectivity of HIV, 2002, J Virol vol. 76, pp. 11440-11446.
Goldhawk et al, Using the magnetosome to model effective gene-based contrast for magnetic resonance imaging, 2012, WIREs Nanomed Nanobiotch vol. 4, pp. 378-388.
Hautot et al, Preliminary observsation of elevated levels of nanocrystalline iron oxide in the basal . . . 2007, Biochim Biophys Acta vol. 1772, pp. 21-25.
Jogler et al, Genetic analysis of magnetosome biomineralization, 2006, Microb Monogr pp. 133-161.
Katzmann et al, Loss of actin-like protein MamK has pleiotropic effects on magnetosome formation . . . 2010, Molc Microb vol. 77, pp. 208-224.
Kirschvink et al., Biogenic magnetite as a basis for magnetic field detection in animals, 1981, Biosystems vol. 13, pp. 181-201.
Kirschvink et al., Magnetite biomineralization in the human brain, 1992, Proc Natl Acad Sci vol. 89, pp. 7683-7687.
Komeli et al., Molecular mechanisms of magnetosome formation, 2007, Ann. Rev. Biochem. vol. 76, pp. 351-366.
Komeli, Molecular mechanisms of compartmentalization and biomineralization in magentotactic bacteria, 2012, FEMS Microb Rev vol. 36, pp. 232-255.
Mannucci et al., Magnetic nanoparticles from Magnetospirillum gryphiswaldense increase the efficacy of thermotherapy . . . 2014, PLoS ONE vol. 9, e108959.
Matsunaga et al, Production of luciferase-magnetic particle complex by recombinant . . . AMB-1, 2000, Biotechnol Bioengin vol. 70, 704-709.
Pradel et al, Biogenesis of actin-like bacaterial cytoskeletal filaments destined for prokaryotic . . . 2006, Proc Natl Acad Sci vol. 103, pp. 17485-17489.
Staniland et al., Controlled cobalt doping of magnetosomes in vivo, 2008, Nature Nanotechnol vol. 3, pp. 158-162.
Tapper et al, Role of lysosomal and cytosolic pH in the regulation of macrophage lysosomal enzyme secretion, 1990, Biochem J vol. 272, pp. 407-414.
Team:NYMU-Taipei-2011.igem.org screenshots of web-site.
Tweten, Cholesterol-dependent cytolysins, a family of versatile pore-forming toxins, 2005, Infect Immun vol. 73, pp. 6199-6209.
Vadia et al., The pore-forming toxin listerolysin O mediates a novel entry pathway of L. monocytogenes into human hepatocytes, 2011, PLoS Pathog vol. 7, e1002356.
Wakeel et al, An Ehrlichia chaffeensis tandem repeat protein interacts with multiple host targets in cell signaling . . . 2009, Infect Immun vol. 77, pp. 1734-1745.
Wakeel et al, Ehrlichia chaffeensis tandem repeat proteins and Ank200 are type 1 secretion system substrates . . . 2011, Front Cell Infect Microb vol. 1, pp. 1-19.
Zurkiya et al, MagA is sufficient for producing magnetic nanoparticles in mammalian cells, making it an MRI reporter, 2008, Magn Reson Med vol. 59, pp. 1225-1231.

\* cited by examiner

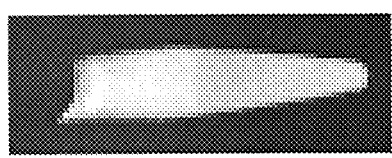
FIG. 4C
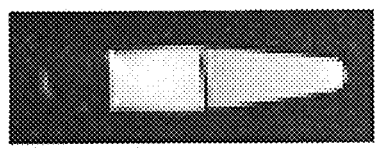
FIG. 4F
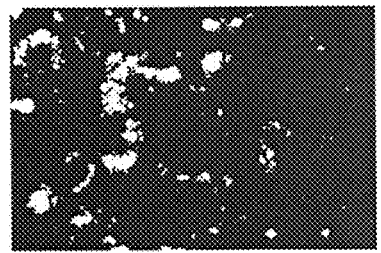
FIG. 4B
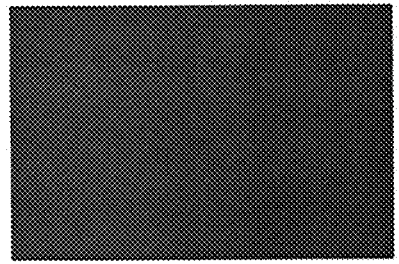
FIG. 4E
FIG. 4A
FIG. 4D

EUKARYOTIC CELLS WITH ARTIFICIAL ENDOSYMBIONTS FOR MULTIMODAL DETECTION

CROSS-REFERENCES TO RELATED APPLICATIONS

This application is a continuation of U.S. application Ser. No. 15/263,144, filed on Sep. 12, 2016, which is a continuation of U.S. application Ser. No. 15/079,453, filed on Mar. 24, 2016, now U.S. Pat. No. 9,446,154, which is a continuation of U.S. application Ser. No. 14/689,987 filed Apr. 17, 2015, now U.S. Pat. No. 9,315,780, which is a continuation of U.S. application Ser. No. 14/332,373 filed Jul. 15, 2014, now U.S. Pat. No. 9,023,612, which is a continuation-in-part of U.S. application Ser. No. 13/838,717, filed Mar. 15, 2013, now U.S. Pat. No. 8,828,681, which is a continuation-in-part of U.S. application Ser. No. 13/374,799, filed on Jan. 13, 2012, now U.S. Pat. No. 8,956,873, and which is a continuation-in-part of PCT/US2013/021414, filed on Jan. 14, 2013, which is a continuation-in-part of U.S. application Ser. No. 13/374,799, filed on Jan. 13, 2012, now U.S. Pat. No. 8,956,873, the entire contents of which applications are hereby incorporated by reference in their entirety for all purposes.

FIELD OF THE INVENTION

The present invention relates generally to the field of endosymbiosis, eukaryotic cells engineered with artificial endosymbionts, and magnetotactic bacteria. In particular, the invention provides single-celled organisms such as artificial endosymbionts, including magnetotactic bacteria, eukaryotic cells to host those single-celled organisms, methods of using eukaryotic cells containing single-celled organisms, and methods of introducing the single-celled organisms into the eukaryotic cells. The invention also provides eukaryotic cells engineered with intracellular single-celled organism allowing multimodal detection of the eukaryotic cells.

BACKGROUND OF THE INVENTION

Mitochondria, chloroplast and other membrane bound organelles add heritable functionalities, such as photosynthesis, to eukaryotic cells. Such organelles (identified by their vestigial circular DNA) are believed to be endosymbiotically derived.

Bacteria exist with a wide range of functionalities not present in various eukaryotic cells. For example, in 1975 Blakemore identified magnetotactic bacteria (MTB) that orient and swim along a geomagnetic field. (Blakemore, R., "Magnetotactic bacteria," *Science* 24:377-379 (1975), which is incorporated by reference in its entirety for all purposes). These magnetotactic bacteria produce magnetic structures called magnetosomes that are composed of magnetite ($Fe_3O_4$) or greigite ($Fe_3S_4$) enclosed by a lipid membrane. (Id.). A large number of MTB species have been identified since their initial discovery. (Id.).

Magnetotactic bacteria have been used to selectively bind to and separate substances. (U.S. Pat. No. 4,677,067, incorporated by reference herein in its entirety for all purposes). Additionally, attempts have been made to add magnetic functionality to cells through external tags. (Swiston, A. J. et al., "Surface Functionalization of Living Cells with Multilayer Patches," *Nano Lett.* 8(12):4446-53 (2008); Vandsburger, M. H. et al., "MRI reporter genes: applications for imaging of cell survival, proliferation, migration and differentiation," *NMR Biomed.* 26(7):872-84 (2013); Ahrens, E. T. et al, "Tracking immune cells in vivo using magnetic resonance imaging," *Nature Rev Immunol.* 13:755-763 (2013); which publications are incorporated by reference in its entirety for all purposes). Bacterial magnetite has also been introduced into red blood cells by cell fusion (Matsunaga, T. and Kamiya, S., (1988), In: Atsumi, K., Kotani, M., Ueno, S., Katila T., Williamsen, S. J. (Eds) 6th International Conference on Biomagnetisms, Tokyo Denki University Press, Tokyo, pp. 50-51 (1988), which is incorporated by reference in its entirety for all purposes), and MTB have been introduced into granulocytes and monocytes by phagocytosis. (Matsunaga, T. et al., "Phagocytosis of bacterial magnetite by leucocytes," *Applied Microbiology and Biotechnology* 31(4):401-405 (1989), which is incorporated by reference in its entirety for all purposes)). However, none of these alterations are heritable to daughter cells.

Currently there is a need in the imaging field for a multimodal probe which can label and track eukaryotic cells with MRI or other types of imaging techniques with minimal manipulation of the host cells. In some embodiments, it is an object of the present invention to provide eukaryotic cells containing a single-celled organism that is introduced into the eukaryotic cell through human intervention which transfers to daughter cells of the eukaryotic cell, in particular through at least five cell divisions, and which maintains sufficient copy number in the daughter cells so that a desired functionality introduced by the single-celled organism is maintained in the daughter cells. It is further an object of the present invention to provide eukaryotic host cells containing artificial endosymbionts that are heritable to daughter cells and methods of uses of these eukaryotic cells. It is also an object of the present invention to provide methods of introducing artificial endosymbionts into the cytosol of eukaryotic host cells. It is another object of the present invention to provide eukaryotic cells with a heritable magnetic phenotype. It is also an object of the invention to provide methods of tracking, localizing, steering, controlling or damaging eukaryotic cells. It is another object of the present invention to provide eukaryotic cells containing a single-celled organism that allows for multimodal detection of the eukaryotic cells. It is a further object of the present invention to provide eukaryotic host cells containing a single-celled organism such that multiple phenotypes are heritable to daughter cells.

SUMMARY OF THE INVENTION

The present invention relates to eukaryotic cells comprising single-celled organisms, such as artificial endosymbionts, methods of using such eukaryotic cells, and methods of introducing such single-celled organisms into eukaryotic cells. In one embodiment, the single-celled organism provides the eukaryotic cell with a desired functionality. In one embodiment, the single-celled organisms are artificial endosymbionts heritable to daughter cells. In another embodiment, the artificial endosymbiont is a magnetotactic bacterium making magnetosomes and expressing another gene product that can be detected. In one embodiment, the magnetotactic bacterium provides the eukaryotic cell with a magnetic functionality. In one embodiment, a method of use is a method of detecting the eukaryotic cells. In another embodiment, a method of use is a method of magnetically manipulating or targeting the eukaryotic cells. In another embodiment, a method of use is a method of damaging the eukaryotic cells. In one embodiment the eukaryotic cells have multiple phenotypes that allow for multimodal detection, which may be introduced to the eukaryotic cell by the single-celled organism. In one embodiment, the multiple phenotypes are heritable to daughter cells of the eukaryotic cells. In one embodiment, the magnetotactic bacterium provides the eukaryotic cell with a magnetic functionality and a light emissive or absorptive property and/or an acoustic property. In an embodiment, the single-celled organism produces a gene product that interacts with a gene product from the eukaryotic cell to produce a detectable signal. In one embodiment, the eukaryotic cell containing the single-celled organism is used in a method of detecting the eukaryotic cells.

In some embodiments, the artificial endosymbiont of the invention may be modified by deleting, adding, and/or mutating at least one gene whereby the artificial endosymbiont acquires a trait useful for endosymbiosis or biotrophy. The genes to be mutated, added, and/or deleted in the artificial endosymbiont may be genes encoding components of the flagellar assembly and genes encoding enzymes for synthesizing essential macromolecules, such as amino acids, nucleotides, vitamins, and co-factors. In certain embodiments, the MTB may further be modified to express an antibiotic resistance gene or other selectable marker. In certain embodiments, the genes localize artificial endosymbionts to specific subcellular locations. In certain embodiments the genes provide enhanced or blocked entry of the artificial endosymbionts to specific host cells. In other embodiments the gene suppresses or alters the host immune system response to the artificial endosymbiont or genes and proteins expressed from it.

In some embodiments the eukaryotic cells of the invention are mammalian, such as mouse, rat, rabbit, hamster, human, porcine, bovine, or canine. In another embodiment, the artificial endosymbiont is transmitted from the host cell to daughter progeny host cells. In another embodiment, the method further comprises deleting, inserting, and/or mutating at least one gene from the eukaryotic cell.

The single-celled organisms of the invention can be introduced into eukaryotic cells by a number of methods known to those of skill in the art including, but not limited to, microinjection, natural phagocytosis, induced phagocytosis, macropinocytosis, other cellular internalization processes, liposome fusion, erythrocyte ghost fusion, or electroporation.

The invention also relates to methods of using multimodal detection to characterize the eukaryotic cell containing the single-celled organism. In the methods of the invention, eukaryotic cells with single-celled organisms have multiple phenotypes that relate to the single-celled organism. In an embodiment, the multiple phenotypes allow for detection of the eukaryotic cells using multimodal observation methods. In an embodiment, multimodal detection is used for non-invasive in vivo imaging of the eukaryotic cells. Each method or modality of imaging can allow visualization of different aspects of anatomy and physiology, and combining these provides greater information about the eukaryotic cells in an in vivo environment.

In an embodiment, multimodal detection of the eukaryotic cell is used for simultaneously acquiring multiple forms of functional data about the cell, and/or enabling detection of the cell on a range of different imaging devices.

BRIEF DESCRIPTION OF THE FIGURES

FIG. 2A shows differential interference contrast (DIC) image and FIG. 2B shows a gray scale fluorescence capture of the same image.

FIGS. 4A-C show images taken of MDA-MB-231 human breast carcinoma cells containing gfp+ AMB-1. FIG. 4A shows a phase contrast image of MDA-MB-231 human breast carcinoma cells containing gfp+ AMB-1. FIG. 4B shows a fluorescence image of the same cells, demonstrating fluorescence signal from the gfp+ AMB-1. FIG. 4C shows a T2w MRI image of a tube filled with agarose (bottom half) and phosphate-buffered saline (top half), with a layer of MDA-MB-231 cells containing gfp+ AMB-1 in between (dark band). FIGS. 4D-F show phase contrast, fluorescence, and MRI images of MDA-MB-231 cells without gfp+ AMB-1.

FIG. 5A is an image of the MDA-MB-231 cells containing gfp+ AMB-1 as seen on visual inspection. FIG. 5B shows an MRI image of the MDA-MB-231 cells containing gfp+ AMB-1. FIG. 5C shows a fluorescence image of the MDA-MB-231 cells containing gfp+ AMB-1.

FIGS. 6A, 6C, 6E, 6G, 6I and 6K are confocal microscope images of the eukaryotic cells containing gfp+ AMB-1; and FIGS. 6B, 6D, 6F, 6H, 6J, and 6L are fluorescence images of the eukaryotic cells containing gfp+ AMB-1.

FIG. 7A is a chart of the luminescence signal obtained from MDA-MB-231 cells with and without lux+ AMB-1. Units of the chart are luminescence per minute. FIG. 7B shows an MRI image of MDA-MB-231 cells containing lux+ AMB-1 (dark band) where the MDA-MB-231 cells containing lux+ AMB-1 are layered on top of an agarose base.

DETAILED DESCRIPTION OF THE INVENTION

Figure 1:
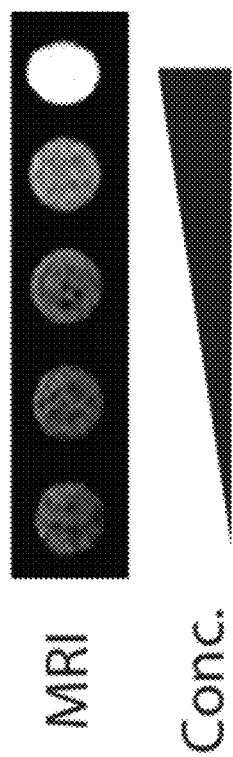
FIG. 1 shows positive contrast generated with a $T_1$ pulse sequence over a log scale concentration up to ~$10^8$ MTB/mL for gfp$^+$AMB-1 suspended in agar plugs using a 1.5T instrument to optimize and characterize the imaging properties.

The invention is illustrated by way of example and not by way of limitation. It should be noted that references to "an"

or "one" or "some" embodiment(s) in this disclosure are not necessarily to the same embodiment, and all such references mean at least one.

It is also to be understood that the singular terms "a", "an", and "the" include plural referents unless context clearly indicates otherwise. Similarly, the word "or" is intended to include "and" (and vice versa) unless the context clearly indicates otherwise. Numerical limitations given with respect to concentrations or levels of a substance are intended to be approximate. Thus, where a concentration is indicated to be at least (for example) 10 µg, it is intended that the concentration be understood to be at least approximately or about 10 µg.

In one aspect, the present invention is directed to eukaryotic cells containing single-celled organisms, such as host cells containing artificial endosymbionts in the cytosol of the host cell, and methods of introducing the single-celled organism into the eukaryotic cell. In one embodiment, the single-celled organism is an artificial endosymbiont that is genetically altered. In some embodiments, the single-celled organisms are magnetotactic bacteria (MTB). The present invention is also directed to eukaryotic cells engineered with a single-celled organism to have multiple phenotypes for detection. Such multiple phenotypes for detection allow multimodal observation of the eukaryotic cells. In an embodiment, multimodal detection of the eukaryotic cells is used for non-invasive in vivo imaging. Each imaging method (or modality) allows the visualization of different aspects of anatomy and physiology, and combining these allows the imager to learn more about the target or subject being imaged.

Definitions

In reference to the present disclosure, the technical and scientific terms used in the descriptions herein will have the meanings commonly understood by one of ordinary skill in the art, unless specifically defined otherwise. Accordingly, the following terms are intended to have the following meanings.

As used herein, the term "AMB" or "AMB-1" refers to *Magnetospirillum magneticum* strain AMB-1.

As used herein, the term "artificial endosymbiont" refers to a single-celled organism which is or has been introduced into the cytosol of a eukaryotic cell through human intervention, and which has been or can be transferred to daughter cells of the eukaryotic cell. In some embodiments, the single-celled organism maintains sufficient copy number in the daughter cells so that a phenotype introduced by the artificial endosymbiont is maintained in the daughter cells.

As used herein, the term "cellular life cycle" refers to series of events involving the growth, replication, and division of a eukaryotic cell. Generally, it can be divided into five stages, known as $G_0$, in which the cell is quiescent, $G_1$ and $G_2$, in which the cell increases in size, S, in which the cell duplicates its DNA, and M, in which the cell undergoes mitosis and divides.

As used herein, the term "cytosol" refers to the portion of the cytoplasm not within membrane-bound sub-structures of the cell.

As used herein, the term "daughter cell" refers to cells that are formed by the division of a cell.

As used herein, the term "essential molecule" refers to a molecule needed by a cell for growth or survival.

As used herein, the term "genetically modified" refers to altering the genetic material of a cell so that a desired property or characteristic of the cell is changed. The term includes introduction of heterologous genetic material into the cell.

As used herein, the term "fluorescent protein" refers to a protein capable of light emission when excited with an appropriate electromagnetic radiation. Fluorescent proteins include proteins having amino acid sequences that are either natural or engineered.

As used herein, the term "bioluminescent protein" refers to a form of chemiluminescence which arises as the result of an energy-yielding chemical reaction in which a specific biochemical substance, for example a luciferin (a naturally occurring fluorophore), is oxidized by an enzyme (e.g., a luciferase) resulting in chemiluminescence.

As used herein, the term "host cell" refers to a eukaryotic cell in which an artificial endosymbiont can reside.

As used herein, the term "image modality" refers to absorption or emission of electromagnetic radiation, acoustic waves, nuclear particles, or other types of energy (e.g., electrical), or a combination thereof, which permits detection or interrogation of the system or target that contains it.

As used herein, the term "intracellular endosymbiont" refers to single-celled organism that spends at least part of its natural life-cycle inside the cells of a eukaryotic organism.

As used herein, the terms "intracellular pathogen" and "intracellular parasite" refer to bacteria that infect a host organism, naturally causes a disease in the host organism, and during the infection some bacteria enter host cells.

As used herein, the term "liposome mediated" refers to artificial vesicles having an aqueous core enclosed in one or more lipid layers, used to convey artificial endosymbionts to host cells.

As used herein, the term "luciferase" refers to a protein that uses a chemical substrate to produce photons. In some embodiments, luciferase refers to an enzyme or photoprotein, such as an oxygenase, that catalyzes a reaction that produces bioluminescence. Luciferases can be recombinant or naturally occurring, or a variant or mutant thereof.

As used herein, the term "magnetosome" refers to particles of a magnetic mineral enclosed by a sheath or membrane, either as individual particles or in chains of particles. In some embodiments, the magnetic mineral in the magnetosome can comprise magnetite (i.e., $Fe_3O_4$) or greigite ($Fe_3S_4$).

As used herein, the term "magnetic bacteria" refers to bacteria that are able to respond to an external magnetic field.

As used herein, the term "magnetotactic bacteria" or "MTB" refers to bacteria with genes encoding magnetosomes.

As used herein, the term "mammal" refers to warm-blooded vertebrate animals all of which possess hair and, in the female, milk producing mammary glands.

As used herein, the term "microinjection" refers to the injection of artificial endosymbionts into host cells.

As used herein, the term "parent cell" refers to a cell that divides to form two or more daughter cells.

As used herein, the term "phenotype" refers to the set of observable characteristics of an organism or cell.

As used herein, the term "receptor mediated" refers to a molecular structure or site on the surface of a host cell that binds with a bacterium or a tagged bacterium followed by internalization of the bacterium.

As used herein, the term "reporter" or "reporter molecule" refers to a moiety capable of being detected indirectly or directly. Reporters include, without limitation, a chromophore, a fluorophore, a fluorescent protein, a receptor, a hapten, an enzyme, and a radioisotope.

As used herein, the term "reporter gene" refers to a polynucleotide that encodes a reporter molecule that can be detected, either directly or indirectly. Exemplary reporter genes encode, among others, enzymes, fluorescent proteins, bioluminescent proteins, receptors, antigenic epitopes, and transporters.

As used herein, the term "reporter probe" refers to a molecule that contains a detectable label and is used to detect the presence (e.g., expression) of a reporter molecule. The detectable label on the reporter probe can be any detectable moiety, including, without limitation, an isotope (e.g., detectable by PET, SPECT, etc), chromophore, and fluorophore. The reporter probe can be any detectable molecule or composition that binds to or is acted upon by the reporter to permit detection of the reporter molecule.

As used herein, the term "heterologous" when used in reference to a nucleic acid or polypeptide refers to a nucleic acid or polypeptide not normally present in nature. Accordingly, a heterologous nucleic acid or polypeptide in reference to a host cell refers to a nucleic acid or polypeptide not naturally present in the given host cell. For example, a nucleic acid molecule containing a non-host nucleic acid encoding a polypeptide operably linked to a host nucleic acid comprising a promoter is considered to be a heterologous nucleic acid molecule. Conversely, a heterologous nucleic acid molecule can comprise an endogenous structural gene operably linked with a non-host (exogenous) promoter. Similarly, a peptide or polypeptide encoded by a non-host nucleic acid molecule, or an endogenous polypeptide fused to a non-host polypeptide is a heterologous peptide or polypeptide.

As used herein, the term "secrete" refers to the passing of molecules or signals from one side of a membrane to the other side.

As used herein, the term "selective agent" refers to a molecule, a polypeptide, or a set of culture conditions that are lethal or inhibitory to a single-celled organism, and/or an artificial endosymbionts, and/or host cells in the absence of a selectable agent.

As used herein, the term "tagged artificial endosymbiont" refers to artificial endosymbionts that have a ligand on the surface of the endosymbiont.

Artificial Endosymbionts

Single-celled organisms of the invention include bacteria that are capable of surviving in a eukaryotic cell and maintain copy number such that the phenotype introduced by the single-celled organism is observed in daughter cells. In some embodiments, the single-celled organism does not kill the eukaryotic host cell without further human intervention. In some embodiments, the single-cell organism has a functionality that is acquired by the eukaryotic cell following the introduction of the single-celled organism. In some embodiments, one or both of the modalities in multimodality provide additional functionality other than just imaging. In some embodiments, the functionality of the single-cell organism is magnetism, production of a nutrient, metabolite, vitamin, cofactor, DNA molecule, RNA molecule, macromolecule, industrial precursor, prodrug, hormone, fatty acid, carbohydrate, simple sugar, signal molecule, pharmacologically active compound, biologically active compound, desalinization, cryoprotectant, nitrogen fixation, photosynthesis, response to environmental challenges, or tolerance to harsh environmental challenges. In some embodiments, the functionality involves expression of a gene in the single-celled organism. In some embodiments, the functionality involves expression of one or more genes or set of genes in the single-celled organism. In some embodiments, the functionality involves expression of a protein in the single-celled organism. In some embodiments the functionality involves expression of a set of proteins in the single-celled organism. In some embodiments, the functionality involves expression of a gene or gene product that is transferred to the host to express the phenotype.

Magnetism includes diamagnetism and paramagnetism. In some embodiments, magnetism includes ferromagnetism. In some embodiments, the eukaryotic cell maintains the functionality for at least 48 hours. In some embodiments, the single-celled organism can stably maintain phenotype in the eukaryotic daughter cells through at least 2 cell divisions, or at least 3 cell divisions, or at least 4 division, or at least 5 divisions, or at least 6, 7, 8, 9, 10, 11, 12, 13, 14, 15, 16, 17, 18, 19, or 20 cell divisions. In another embodiment, the single-celled organism can stably maintain phenotype in the eukaryotic daughter cells through 3-5 divisions, or 5-10 divisions, or 10-15 divisions, or 15-20 divisions.

In some embodiments, the single-celled organisms of the invention are genetically modified. Methods for genetically modifying bacteria are well known in the art. In some embodiments, the bacteria will be genetically modified to improve their survival in eukaryotic host cells, and/or to reduce the toxicity of the single-celled organism to the eukaryotic cell, and/or to provide the eukaryotic cell with a useful phenotype. In one embodiment, the flagellar proteins of a single-celled organism are modified so that the single-celled organism no longer expresses flagellar proteins in the eukaryotic host cell. In another embodiment, the single-celled organism is modified so that it can no longer synthesize an essential molecule that is preferably provided by the eukaryotic host cell. In an embodiment, the single-celled organism is genetically modified so that its cell cycle is coordinated with the cell cycle of the eukaryotic host cell so that copy number of the single-celled organism can be maintained at a sufficient level to impart the phenotype to daughter cells. In some embodiments, the genes localize artificial endosymbionts to specific subcellular locations. In certain embodiments, the genes provide enhanced or blocked entry of the artificial endosymbionts to specific host cells. In some embodiments, the gene suppresses or alters the host immune system response to the artificial endosymbiont or genes and proteins expressed from it.

Embodiments of the invention include single-celled organisms that are α-Proteobacteria. In the current taxonomic scheme based on 16S rRNA, α-proteobacteria are recognized as a Class within the phylum Proteobacteria, and are subdivided into 7 main subgroups or orders (Caulobacterales, Rhizobiales, Rhodobacterales, Rhodospirillales, Rickettsiales, Sphingomonadales and Parvularculales). (Gupta, R. S., "Phylogenomics and signature proteins for the alpha Proteobacteria and its main groups," *BMC Microbiol.* 7:106 (2007), incorporated herein by reference in its entirety for all purposes).

A large number of α-proteobacterial genomes that cover all of the main groups within α-proteobacteria have been sequenced, providing information that can be used to identify unique sets of genes or proteins that are distinctive characteristics of various higher taxonomic groups (e.g., families, orders, etc.) within α-proteobacteria. (Gupta, supra; incorporated herein by reference in its entirety for all purposes).

Single celled organisms useful as artificial endosymbionts include, by way of example and not limitation, *Anabaena, Nostoc, Diazotroph, Cyanobacteria, Trichodesmium, Beijerinckia, Clostridium*, Green sulfur bacteria, Azotobacteraceae, *Rhizobia, Frankia, flavobacteria, Methanosarcinales,* aerobic halophilic Archaea of the order Halobacteriales, the fermentative anerobyves of the order Halanaerobiales (low G+C brand of the Firmicutes), the red aerobic *Salinibacter* (Bacteroidetes branch), *Marinobacter, Halomonas, Dermacoccus, Kocuria, Micromonospora, Streptomyces, Williamsia, Tskamurella, Alteromonas, Colwellia, Glaciecola, Pseudoalteromonas, Shewanella, Polaribacter, Pseudomonas, Psychrobacter, Athrobacter, Frigoribacterium, Subtercola, Microbacterium, Rhodoccu, Bacillus, Bacteroides, Propionibacterium, Fusobacterium, Klebsiella,* lecithinase-positive *Clostridia, Veillonella,* Fusobacteria, Chromatiaceae, Chlorobiceae, Rhodospirillaceae, thiobacilli, *nitrosomonas, nitrobacter,* methanogens, acetogens, sulfate reducers, and lactic acid bacteria.

The genomes of a number of these single celled organisms have been or are being sequenced, including for example: *M. frigidum, M. burtonii, C. symbiosum, C. psychrerythraea, P. haloplanktis, Halorubrum lacusprofundi, Vibrio salmonicida, Photobacterium profundum, S. violacea, S. frigidimarina, Psychrobacter* sp. 273-4, *S. benthica, Psychromonas* sp. CNPT3, *Moritella* sp., *Desulfotalea Psychrophila, Exiguobacterium* 255-15, *Flavobacterium psychrophilum, Psychroflexus torquis, Polaribacter filamentous, P. irgensii, Renibacterium salmoninarum, Leifsonia*-related PHSC20-c1, *Acidithiobacillus ferrooxidans, Thermoplasma acidophilum, Picrophilus torridus, Sulfolobus tokodaii,* and *Ferroplasma acidarmanus.*

In an embodiment, artificial endosymbionts exclude single-celled organisms that are known to be intracellular pathogens or intracellular endosymbionts. The genomes of many intracellular pathogens include genomic islands containing virulence genes encoding, for example, adherence factors that allow the intracellular pathogen to attach to target eukaryotic cells, and trigger phagocytosis of the intracellular pathogen. (Juhas, M. et al., "Genomic islands: tools of bacterial horizontal gene transfer and evolution," *FEMS Microbiol Rev.* 33:376-393 (2009), incorporated herein by reference in its entirety for all purposes). Many virulence factors utilize type III or type IV secretion systems. Some virulence factors are secreted into the eukaryotic host cell and alter membrane traffic within the target eukaryotic cell, some virulence factors interact with host proteins involved in apoptosis. (Dubreuil, R. et al., "Bringing host-cell takeover by pathogenic bacteria to center stage," *Cell Logis.* 1:120-124 (2011), incorporated herein by reference in its entirety for all purposes).

Embodiments of the invention include single-celled organisms that are magnetotactic bacteria ("MTB"). A large number of MTB species are known to those of ordinary skill in the art since their initial discovery in 1975 by Blakemore (see, e.g., Blakemore, R., "Magnetotactic bacteria," *Science* 24: 377-379 (1975), incorporated herein by reference in its entirety for all purposes) and represent a group of microbes (Faivre, D. et al., "Magnetotactic bacteria and magnetosomes," *Chem Rev.* 108:4875-4898 (2008), incorporated herein by reference in its entirety for all purposes). MTB have been identified in different subgroups of the Proteobacteria and the Nitrospira phylum with most of the phylotypes grouping in α-Proteobacteria. Currently, culturable MTB strains assigned as α-Proteobacteria by 16S rRNA sequence similarity include the strain originally isolated by Blakemore in 1975, *Magnetospirillum magnetotactium* (formerly *Aquasprillium magnetotactium*), *M. gryphiswaldense, M. magneticum* strain AMB-1 ("AMB"), *M. polymorphum, Magnetospirillum* sp. MSM-4 and MSM-6, *Magnetococcus marinus,* marine *vibrio* strains MV-1 and MV-2, a marine spirillum strain MMS-1 and *Magnetococcus* sp. strain MC-1, as well as others. A number of MTB are available in pure culture, including AMB. The doubling time of AMB in pure culture is approximately eight hours and is close to that of a typical mammalian cell.

Standard MTB growth media uses succinic acid as the main carbon source, but MTB can be grown with fumarate, tartrate, malate, lactate, pyruvate, oxaloacetate, malonate, P-hydroxybutyrate and maleate as the sole carbon source. These metabolites are present inside eukaryotic cells. Microaerophillic, facultative anaerobic, and obligate anaerobic MTB strains have been identified. Oxygen concentrations in the cytosol of eukaryotic cells are low due to sequestration by proteins such as myoglobin and concentration in specific cellular locations, e.g., mitochondria, thus the microaerophilic or facultative anaerobic environment necessary for MTB growth is already present in a eukaryotic cell.

MTBs can also be classified by the magnetic particles they synthesize, either magnetite ($Fe_3O_4$) or greigite ($Fe_3S_4$). Magnetite producers are microaerophilic or facultative anaerobic, need some oxygen source for magnetosome synthesis, and have optimal growth temperatures near physiological temperature.

In some embodiments, the single-celled organisms of the invention are genetically modified. Molecular biology tools have been developed for genetic manipulations of MTB most extensively in AMB and *M. gryphiswaldense* strain MSR-1 (reviewed in Jogler, C. and Schtiler, D., in "Magnetoreception and Magnetosomes in Bacteria," p 134-138, New York, Springer (2007), incorporated herein by reference in its entirety for all purposes). Because the genome of AMB was the first sequenced of any MTB, all MTB gene references herein refer to this genome unless otherwise specified. The genomes of two other *Magnetospirillum* strains and *Magnetococcus* sp. strain MC-1 have also been recently sequenced. Genes from these strains or other MTB strains, presently culturable or unculturable, sequenced or unsequenced, known or unknown, can be used in the present invention.

The genes responsible for magnetosome formation in MTB cluster in genomic islands, known as the magnetosome island (MAI). In *M. gryphiswaldense*, the 130 kb MAI is generally structured into four polycistronic operons: the mamAB operon has 17 identified ORFs extending over 16.4 kb; the mamGFDC operon has 4 identified ORFs, 2.1 kb and 15 kb upstream of mamAB; the mms6 operon has 6 identified ORFs, 3.6 kb and 368 bp upstream of the mamGFDC; the mamXY operon has 4 identified ORFs located about 30 kb downstream of mamAB; and the monocistronic mamW gene. In the MaI, the proteins Mam W, Mg1457, Mg1458, Mg1459, Mms6, Mg1462, MamG, MamF, MamD, MamC, MamH, MamI, MamE, MamJ, MamK, MamL, MamM, MamN, MamO, MamP, MamA, MamQ, MamR, MamB, MamS, MamT, MamU, and Mg1505 have been identified, many of which have been given specific functions in magnetosome formation. Four genes outside the MAI have been linked to magnetosome formation, mamY, mtxA, mmsF and mamX Conserved MAI's have been found in other MTB with some differences in genomic organization and size. These genes have also been identified for AMB-1. (See Table 2 in Fukuda, Y. et al., "Dynamic analysis of a genomic island in *Magnetospirillum* sp. Strain AMB-1 reveals how magnetosome synthesis developed," *FEBS Lett.* 580:801-812 (2006), incorporated herein by reference in its entirety for all purposes).

In some embodiments, genetic modifications are made to the single-celled organism. Such modifications can be directed modifications, random mutagenesis, or a combination thereof. Natural endosymbionts are donors of novel capabilities and often derive nutritional requirements from the host.

Natural colonization of a host by the symbionts occurs in seven stages: 1) transmission, 2) entry, 3) countering of host defense, 4) positioning, 5) providing advantage to the host, 6) surviving in host environment, and 7) regulation.

In some embodiments, mutual nutritional dependence (biotrophy) may be established between the single-celled organism and the eukaryotic cell. In one embodiment, the single-celled organism comprises at least one deletion or inactivation of a gene encoding an enzyme for synthesizing an essential molecule, thereby resulting in absence of enzyme or expression of inactive enzyme, wherein said essential molecule is produced by the eukaryotic host cell. An essential molecule can include, but is not limited to, an amino acid, a vitamin, a cofactor, and a nucleotide. For instance, biotrophy can be accomplished by knocking-out the ability of the single-celled organism to make an amino acid, which will then be derived from the host. Glycine is a reasonable choice as it is highly abundant in mammalian cells and a terminal product in bacterial amino acid biogenesis; at least 22 other possibilities exist. The enzyme serine hydroxymethyltransferase converts serine into glycine at the terminus of the 3-phosphoglycerate biosynthetic pathway for amino acid production. In one embodiment, the single-celled organism is an AMB in which the gene amb2339 (which encodes the enzyme serine hydroxymethyltransferase) is genetically modified. There are numerous methods for mutating or knocking-out genes known to those of ordinary skill in the art, including in vitro mutagenesis, targeted insertion of DNA into the gene of interest by homologous recombination or deletion of the gene (or operon, as most of the genes in the bacteria cluster in operons), or using endonucleases provided appropriate sites only around the target are present in the genome.

In another embodiment, nutritional dependence for a single-celled organism on the host cell could also be established by eliminating the ability of the single-celled organism to synthesize various metabolites, cofactors, vitamins, nucleotides, or other essential molecules.

In some embodiments of the invention, an MTB has mutations and/or deletions in genes associated with mobility and/or secretion. MTB are flagellated, and in some embodiments of the invention, the MTB has a deletion and/or mutation in at least one gene encoding molecular machinery associated with the flagella such that the magnetic bacterium does not produce a functional flagellum. Additionally, many MTB secrete various compounds, such as hydroxamate and catechol siderophores, which may be detrimental to or elicit an immune response from the host. In the sequenced genome of AMB, of the 4559 ORF's, 83 genes have been related to cell mobility and secretion. The flagellar assembly is known to be composed of the gene products of amb0498, amb0500, amb0501, amb0502, amb0503, amb0504, amb0505, amb0610, amb0614, amb0615, amb0616, amb0617, amb0618, amb0619, amb0628, amb1289, amb1389, amb2558, amb2559, amb2578, amb2579, amb2856, amb3493, amb3494 amb3495, amb3496, amb3498, amb3824, and amb3827. The flagella is controlled by the chemotaxis machinery, which is composed of at least the gene products of amb0322, amb0323, amb0324, amb0325, amb0326, amb1806, amb1963, amb1966, amb2333, amb2635, amb2640, amb2648, amb2652, amb2826, amb2932, amb3002, amb3003, amb3004, amb3007, amb3102, amb3329, amb3501, amb3502, amb3654, amb3879, and amh3880.

In one embodiment, genes encoding antibiotic resistance are inserted into the genome of the single-celled organism. Eukaryotic cells cultured in media containing the antibiotic will require the single-celled organism for survival. Neomycin resistance is conferred by either one of two aminoglycoside phosphotransferase genes, which also provide resistance against geneticin (G418), a commonly used antibiotic for eukaryotes. Hygromycin B resistance is conferred by a kinase that inactivates hygromycin B by phosphorylation. Puromycin is a commonly used antibiotic for mammalian cell culture, and resistance is conferred by the pac gene encoding puromycin N-acetyl-transferase. External control of the antibiotic concentration allows intracellular regulation of the copy number of the single-celled organism. Any other system where resistance or tolerance to an external factor is achieved by chemical modification of this factor can also be employed. An indirect nutritive advantage on eukaryotic cells may also be established by using MTB and a magnetic culture method. In this embodiment, magnetic fields are established to confer an advantage to eukaryotic cells containing MTB. This could be either by providing the means for attachment to culture matrix, access to necessary growth or media factors or by selection between cell passages.

In another embodiment, genetic modifications are made in the MTB genome to enhance intracellular stability against the host defense mechanisms for a particular host cell type. Many eukaryote endosymbionts and endoparasites, such as the proteobacterial endosymbionts of insects such as *Buchnera, Wigglesworthia*, and *Wolhachia*; the methanogenic endosymbionts of anaerobic ciliates; the nitrogen-fixing symbionts in the diatom *Rhopalodia*; the chemosynthetic endosymbiont consortia of gutless tubeworms (*Olavius* or *Jnanidrillus*); the cyanobacterial endosymbionts of sponges; the endosymbionts of all five extant classes of Echinodermata; the *Rhizobia* endosymbionts of plants; various endosymbiotic algae; the *Legionella*-like X bacteria endosymbionts of *Ameoba proteus*; numerous *Salmonella* sp., *Mycobacterium tuberculosis, Legionella pneumophila*, etc. reside in membrane-bound vacuoles often termed symbiosomes, while some species, such as *Blochmannia*, the *rickettsia, Shigella*, enteroinvasive *Escherichia coli*, and *Listeria*, have the ability to inhabit the cytosol. The Dot-Icm Type IV secretory system is employed by many intracellular bacteria acquired by phagocytosis to evade the endocytic pathway and persist in the host cell. This system has been well-studied in *L. pneumophila* and consists of the proteins: DotA through DotP, DotU, DotV, IcmF, IcmQ through IcmT, IcmV, IcmW and IcmX. In *Photorhabdus luminescens*, the luminescent endosymbiont of nematodes, the genes encoding RTX-like toxins, proteases, type III secretion system and iron uptake systems were shown to support intracellular stability and replication. The gene bacA and the regulatory system BvrRS are essential for maintenance of symbiosis between *Rhizobia* and plants as well as the survival of *Brucella ahortus* in mammalian cells. The PrfA regulon enables some *Listeria* species to escape the phagesome and inhabit the cytosol. The desired cellular location (e.g., symbiosome or cytosol) of the intracellular MTB will dictate which genes are required to be expressed in the MTB (either directly from the genome or through a stable vector) for survival and proliferation in the host environment. The endogenous plasmid pMGT is highly stable in MTB and a number of other broad range vectors (including those of IncQ, IncP, pBBR1, etc.) are capable of stable replication in MTB.

In another embodiment, the single-celled organism is genetically modified by knocking in genes, such as bacteriostatic gene(s), siderophore gene(s), metabolic requirement gene(s), suicide gene(s), life cycle regulation gene(s), transporter gene(s), and escape from the phagosome gene(s). In another embodiment, the single-celled organisms are randomly mutated and subsequently screened for enhanced integration within the host cell. Random mutation can be accomplished by treatment with mutagenic compounds, exposure to UV-light or other methods know to those skilled in the art.

In another embodiment, transgenetic modification(s) are made to counter eukaryotic cell defenses using genes from various parasites or endosymbionts. In another embodiment, the population of the single-celled organisms in the eukaryotic host cell is regulated though a balance of intrinsic use of host mechanisms (nutrient availability, control of reproduction, etc.) and antibiotic concentration.

In another embodiment, a natural endosymbiont or an intracellular parasite is genetically modified to produce magnetosomes. Endosymbionts of insects such as *Buchnera, Wigglesworthia*, and *Wolbachia*; the methanogenic endosymbionts of anaerobic ciliates; the nitrogen-fixing symbionts in the diatom *Rhopalodia*; the chemosynthetic endosymbiont consortia of gutless tubeworms (*Olavius* or *lnanidrillus*); the cyanobacterial endosymbionts of sponges; the endosymbionts of all five extant classes of Echinodermata; the *Rhizobia* endosymbionts of plants; various endosymbiotic algae; the *Legionella*-like X bacteria endosymbionts of *Ameoba proteus*, numerous *Salmonella* sp., *Mycobacterium tuberculosis, Legionella pneumophila* belonging to α-proteobacteria could be genetically engineered to produce magnetosomes. In another embodiment, a pre-existing organelle can be genetically modified to express one or more magnetosome genes to produce an artificial endosymbiont. For instance, mitochondria, plastids, hydrogenosomes, apicoplasts or other organelles, which harbor their own genetic material, can be genetically altered. Bacteria modified to produce magnetosomes may include *Francisella tularensis, Listeria monocytogenes, Salmonella typhi, Brucella, Legionella, Mycobacterium, Nocardia, Rhodococcus equi, Yersinia, Neisseria meningitidis, Chlamydia, Rickettsia, Coxiella* and the like.

In a preferred embodiment, the single-celled organism is an MTB, which may or may not be genetically altered, that produces magnetic particles upon culturing of the eukaryotic cells.

Nucleic Acids

The nucleic acids of the invention can include expression vectors, such as plasmids, or viral vectors, or linear vectors, or vectors that integrate into chromosomal DNA. Expression vectors can contain a nucleic acid sequence that enables the vector to replicate in one or more selected host cells. Such sequences are well known for a variety of cells. The origin of replication from the plasmid pBR322 is suitable for most Gram-negative bacteria. In eukaryotic host cells, e.g., mammalian cells, the expression vector can be integrated into the host cell chromosome and then replicate with the host chromosome. Similarly, vectors can be integrated into the chromosome of prokaryotic cells.

Expression vectors also generally contain a selection gene, also termed a selectable marker. Selectable markers are well-known in the art for prokaryotic and eukaryotic cells, including host cells of the invention. This selection gene encodes a protein necessary for the survival or growth of transformed host cells grown in a selective culture medium. Host cells not transformed with the vector containing the selection gene will not survive in the culture medium. Typical selection genes encode proteins that (a) confer resistance to antibiotics or other toxins, e.g., ampicillin, neomycin, methotrexate, or tetracycline; (b) complement auxotrophic deficiencies; or (c) supply critical nutrients not available from complex media, e.g., the gene encoding D-alanine racemase for Bacilli. One example of a selection scheme utilizes a drug to arrest growth of a host cell. Those cells that are successfully transformed with a heterologous gene produce a protein conferring drug resistance and thus survive the selection regimen. Other selectable markers for use in bacterial or eukaryotic (including mammalian) systems are well-known in the art. In some embodiments, the selectable marker is the target protein or encoded by the nucleic acid secreted by the single-celled organism into the host cell.

The expression vector for producing a heterologous polypeptide may also contain an inducible promoter that is recognized by the host RNA polymerase and is operably linked to the nucleic acid encoding the target protein. Inducible or constitutive promoters (or control regions) with suitable enhancers, introns, and other regulatory sequences are well-known in the art.

In some embodiments, it may be desirable to modify the polypeptides of the invention. One of skill will recognize many ways of generating alterations in a given nucleic acid construct. Such well-known methods include site-directed mutagenesis, PCR amplification using degenerate oligonucleotides, exposure of cells containing the nucleic acid to mutagenic agents or radiation, chemical synthesis of a desired oligonucleotide (e.g., in conjunction with ligation and/or cloning to generate large nucleic acids) and other well-known techniques. See, e.g., Giliman and Smith, *Gene* 8:81-97 (1979) and Roberts et al., *Nature* 328: 731-734 (1987), incorporated herein by reference.

In some embodiments, the recombinant nucleic acids encoding the polypeptides of the invention are modified to provide preferred codons which enhance translation of the nucleic acid in a selected organism.

The polynucleotides of the invention also include polynucleotides, including nucleotide sequences that are substantially equivalent to the polynucleotides of the invention. Polynucleotides according to the invention can have at least about 80%, more typically at least about 90%, and even more typically at least about 95%, sequence identity to a polynucleotide of the invention. The invention also provides the complement of the polynucleotides including a nucleotide sequence that has at least about 80%, more typically at least about 90%, and even more typically at least about 95%, sequence identity to a polynucleotide encoding a polypeptide recited above. The polynucleotide can be DNA (genomic, cDNA, amplified, or synthetic) or RNA. Methods and algorithms for obtaining such polynucleotides are well known to those of skill in the art and can include, for example, methods for determining hybridization conditions which can routinely isolate polynucleotides of the desired sequence identities.

Nucleic acids which encode protein analogs in accordance with this invention (i.e., wherein one or more amino acids are designed to differ from the wild type polypeptide) may be produced using site directed mutagenesis or PCR amplification in which the primer(s) have the desired point mutations. For a detailed description of suitable mutagenesis techniques, see Sambrook et al., Molecular Cloning: A Laboratory Manual, Cold Spring Harbor Laboratory Press, Cold Spring Harbor, N.Y. (1989), and/or Ausubel et al., editors, Current Protocols in Molecular Biology, Green Publishers Inc. and Wiley and Sons, N.Y. (1994). Chemical synthesis using methods described by Engels et al., 1989, in Angew. Chem. Intl. Ed., Volume 28, pages 716-734, may also be used to prepare such nucleic acids.

"Recombinant variant" refers to any polypeptide differing from naturally occurring polypeptides by amino acid insertions, deletions, and substitutions, created using recombinant DNA techniques. Guidance in determining which amino acid residues may be replaced, added, or deleted without abolishing activities of interest, such as enzymatic or binding activities, may be found by comparing the sequence of the particular polypeptide with that of homologous peptides and minimizing the number of amino acid sequence changes made in regions of high homology.

Preferably, amino acid "substitutions" are the result of replacing one amino acid with another amino acid having similar structural and/or chemical properties, i.e., conservative amino acid replacements. Amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

"Insertions" or "deletions" are typically in the range of about 1 to 5 amino acids. The variation allowed may be experimentally determined by systematically making insertions, deletions, or substitutions of amino acids in a polypeptide molecule using recombinant DNA techniques and assaying the resulting recombinant variants for activity.

Alternatively, where alteration of function is desired, insertions, deletions or non-conservative alterations can be engineered to produce altered polypeptides or chimeric polypeptides. Such alterations can, for example, alter one or more of the biological functions or biochemical characteristics of the polypeptides of the invention. For example, such alterations may change polypeptide characteristics such as ligand-binding affinities or degradation/turnover rate. Further, such alterations can be selected so as to generate polypeptides that are better suited for expression, scale up and the like in the host cells chosen for expression.

Alternatively, recombinant variants encoding these same or similar polypeptides may be synthesized or selected by making use of the "redundancy" in the genetic code. Various codon substitutions, such as the silent changes which produce various restriction sites, may be introduced to optimize cloning into a plasmid or viral vector or expression in a particular prokaryotic or eukaryotic system. Mutations in the polynucleotide sequence may be reflected in the polypeptide or domains of other peptides added to the polypeptide to modify the properties of any part of the polypeptide, to change characteristics such as ligand-binding affinities, or degradation/turnover rate.

In a preferred method, polynucleotides encoding the novel nucleic acids are changed via site-directed mutagenesis. This method uses oligonucleotide sequences that encode the polynucleotide sequence of the desired amino acid variant, as well as a sufficient adjacent nucleotide on both sides of the changed amino acid to form a stable duplex on either side of the site of being changed. In general, the techniques of site-directed mutagenesis are well known to those of skill in the art, and this technique is exemplified by publications such as, Edelman et al., *DNA* 2:183 (1983). A versatile and efficient method for producing site-specific changes in a polynucleotide sequence is described in Zoller and Smith, *Nucleic Acids Res.* 10:6487-6500 (1982).

PCR may also be used to create amino acid sequence variants of the nucleic acids. When small amounts of template DNA are used as starting material, primer(s) that differs slightly in sequence from the corresponding region in the template DNA can generate the desired amino acid variant. PCR amplification results in a population of product DNA fragments that differ from the polynucleotide template encoding the target at the position specified by the primer. The product DNA fragments replace the corresponding region in the plasmid and this gives the desired amino acid variant.

A further technique for generating amino acid variants is the cassette mutagenesis technique described in Wells et al., *Gene* 34:315 (1985), and other mutagenesis techniques well known in the art, such as, for example, the techniques in Sambrook et al., supra, and Ausubel et al., supra.

Eukaryotic Cells

In some embodiments, the invention provides eukaryotic cells comprising single-celled organisms in the eukaryotic cells that are heritable and methods of introducing the single-celled organisms into host cells.

In some embodiments, the eukaryotic cells are plant cells. In some embodiments the eukaryotic cells are cells of monocotyledonous or dicotyledonous plants, including, but not limited to, maize, wheat, barley, rye, oat, rice, soybean, peanut, pea, lentil and alfalfa, cotton, rapeseed, canola, pepper, sunflower, potato, tobacco, tomato, eggplant, *eucalyptus*, a tree, an ornamental plant, a perennial grass, or a forage crop. In other embodiments, the eukaryotic cells are algal, including but not limited to algae of the genera *Chlorella, Chlamydomonas, Scenedesmus, Isochrysis, Dunaliella, Tetraselmis, Nannochloropsis,* or *Prototheca*, In some embodiments, the eukaryotic cells are fungi cells, including, but not limited to, fungi of the genera *Saccharomyces, Klyuveromyces, Candida, Pichia, Debaromyces, Hansenula, Yarrowia, Zygosaccharomyces,* or *Schizosaccharomyces*.

In some embodiments, the eukaryotic cells of the invention are animal cells. In some embodiments the eukaryotic cells are mammalian, such as mouse, rat, rabbit, hamster, human, porcine, bovine, or canine. Mice routinely function as a model for other mammals, most particularly for humans. (See, e.g., Hanna, J. et al., "Treatment of sickle cell anemia mouse model with iPS cells generated from autologous skin," *Science* 318:1920-1923 (2007); Holtzman, D. M. et al., "Expression of human apolipoprotein E reduces amyloid-β deposition in a mouse model of Alzheimer's disease," *J Clin Invest.* 103(6):R15-R21 (1999); Warren, R. S., et al., "Regulation by vascular endothelial growth factor of human colon cancer tumorigenesis in a mouse model of experimental liver metastasis," *J Clin Invest.* 95:1789-1797 (1995); each of which is incorporated herein by reference in its entirety for all purposes).

In some embodiments, the eukaryotic cell is a human cancer cell. There are many human cancer cell lines that are well known to those of ordinary skill in the art, including common epithelial tumor cell lines such as Coco-2, MDA-MB-231 and MCF7; and non-epithelial tumor cell lines, such as HT-1080 and HL60, and the NCI60-cell line panel (see, e.g., Shoemaker, R., "The NCI60 human tumor cell line anticancer drug screen," *Nat Rev Cancer* 6:813-823 (2006), incorporated herein by reference in its entirety for all purposes). Additionally, those of ordinary skill in the art are familiar with obtaining cancer cells from primary human tumors.

In other embodiments, the eukaryotic cells are stem cells. Those of ordinary skill in the art are familiar with a variety of stem cell types, including Embryonic Stem Cells, Inducible Pluripotent Stem Cells, Hematopoietic Stem Cells, Neural Stem Cells, Epidermal Neural Crest Stem Cells, Mammary Stem Cells, Intestinal Stem Cells, Mesenchymal stem cells, Olfactory adult stem cells, and Testicular cells.

In an embodiment, the eukaryotic cell is a cell found in the circulatory system of a human host. For example, red blood cells, platelets, plasma cells, T-cells, natural killer cells, or the like, and precursor cells of the same. As a group, these cells are defined to be circulating host cells of the invention. The present invention may be used with any of these circulating cells. In an embodiment, the eukaryotic host cell is a T-cell. In another embodiment, the eukaryotic cell is a B-cell. In an embodiment, the eukaryotic cell is a neutrophil. In an embodiment, the eukaryotic cell is a megakaryocyte.

In another embodiment, at least one gene from the eukaryotic cell is genetically altered. In some embodiments, mutual nutritional dependence (biotrophy) may be established between the artificial endosymbiont and the eukaryotic cell by genetic modification of the eukaryotic cell, using the appropriate molecular biology techniques specific to the target host cell type known to those of ordinary skill in the art, creating eukaryotic cell dependence on the single-celled organism for some essential macromolecule thus establishing the environmental pressures for biotrophy. In another embodiment, nutritional dependence for a single-celled organism on the eukaryotic cell may be established by genetically altering the single-celled organism to eliminate the ability of it to synthesize various metabolites, cofactors, vitamins, nucleotides, or other essential molecules. In such embodiments, the essential molecule may be provided by the single-celled organism. In another embodiment, the eukaryotic cell gene encoding the enzyme serine hydroxymethyltransferase, which converts serine into glycine at the terminus of the 3-phosphoglycerate biosynthetic pathway for amino acid production, may be modified.

Methods of Introducing Single-Celled Organisms into Eukaryotic Cells

The single-celled organisms of the invention can be introduced into eukaryotic cells by a number of methods known to those of skill in the art including, but not limited to, microinjection, natural phagocytosis, induced phagocytosis, macropinocytosis, other cellular uptake processes, liposome fusion, erythrocyte ghost fusion, electroporation, receptor mediated methods, and the like (see, e.g., Microinjection and Organelle Transplantation Techniques, Celis et al. Eds., Academic Press: New York, (1986), and references cited therein; incorporated herein by reference in its entirety for all purposes).

In one embodiment, a single-celled organism is introduced to the host cell by microinjection into the cytoplasm of the host cell. A variety of microinjection techniques are known to those skilled in the art. Microinjection is the most efficient of transfer techniques available (essentially 100%) and has no cell type restrictions (Id.; Xi, Z. et al., "Characterization of *Wolbachia* transfection efficiency by using microinjection of embryonic cytoplasm and embryo homogenate," *Appl Environ Microbiol.* 71(6):3199-3204 (2005); Goetz, M. et al., "Microinjection and growth of bacteria in the cytosol of mammalian host cells," *Proc Natl Acad. Sci. USA* 98:12221-12226 (2001); all publications incorporated herein by reference in its entirety for all purposes).

Naturally phagocytotic cells have been show to take up bacteria, including MTB (Burdette, D. L. et al., *Vibrio* VopQ induces PI3-kinase independent autophagy and antagonizes phagocytosis," *Mol Microbiol.* 73:639 (2009); Wiedemann, A. et al., "*Yersinia enterocolitica* invasin triggers phagocytosis via β1 integrins, CDC42Hs and WASp in macrophages," *Cell Microbiol.* 3:693 (2001); Hackam, D. J. et al., "Rho is required for the initiation of calcium signaling and phagocytosis by Fcγ receptors in macrophages," *J Exp Med.* 186(6):955-966 (1997); Matsunaga, T. et al., "Phagocytosis of bacterial magnetite by leucocytes," *Appl Microbiol Biotechnol.* 31(4):401-405 (1989); all publications incorporated herein by reference in its entirety for all purposes).

This method is scalable, but may be limited to specific cell types (e.g., macrophage). However, recent studies have shown that non-phagocytotic cell types can be induced to endocytose bacteria when co-cultured with various factors: media and chemical factors, and biologic factors (e.g., baculovirus, protein factors, genetic knock-ins, etc.). (See, e.g., Salminen, M., et al., "Improvement in nuclear entry and transgene expression of baculoviruses by disintegration of microtubules in human hepatocytes," *J Virol.* 79(5):2720-2728 (2005); Modalsli, K. R. et al., "Microinjection of HEp-2 cells with coxsackie B1 virus RNA enhances invasiveness of *Shigella flexneri* only after prestimulation with UV-inactivated virus," APMIS 101:602-606 (1993); Hayward, R. D. et al., "Direct nucleation and bundling of actin by the SipC protein of invasive *Salmonella,*" *EMBO J.* 18:4926-4934 (1999); Yoshida, S. et al., "*Shigella* deliver an effector protein to trigger host microtubule destabilization, which promotes Rac1 activity and efficient bacterial internalization," *EMBO J.* 21:2923-2935 (2002); Bigildeev et al. *J Exp Hematol.* 39:187 (2011); Finlay, B. B. et al., Common themes in microbial pathogenicity revisited," *Microbiol Mol Biol Rev.* 61:136-169 (1997); all publications are incorporated herein by reference in its entirety for all purposes).

The related process, macropinocytosis or "cell drinking," is a method numerous bacteria and viruses employ for intracellular entry (Zhang (2004) In: Molecular Imaging and Contrast Agent Database (MICAD) (database online); Bethesda (Md.): National Library of Medicine (US), NCBI; 2004-2011; both publications incorporated by reference in its entirety for all purposes). Various protocols exist which can be employed to induce cells to take up bacteria. Several agents, such as nucleic acids, proteins, drugs and organelles have been encapsulated in liposomes and delivered to cells (Ben-Haim, N. et al., "Cell-specific integration of artificial organelles based on functionalized polymer vesicles," *Nano Lett.* 8(5):1368-1373 (2008); Lian, W. et al., "Intracellular delivery can be achieved by bombarding cells or tissues with accelerated molecules or bacteria without the need for carrier particles," *Exp Cell Res.* 313(1):53-64 (2007); Heng, B. C. et al., "Immunoliposome-mediated delivery of neomycin phosphotransferase for the lineage-specific selection of differentiated/committed stem cell progenies: Potential advantages over transfection with marker genes, fluorescence-activated and magnetic affinity cell-sorting," *Med Hypotheses* 65(2):334-336 (2005); Potrykus, Ciba Found Symp, Vol. 1 54:198 (1990); all publications incorporated herein by reference in its entirety for all purposes). This method is inexpensive, relatively simple and scalable. Additionally, liposome uptake can be enhanced by manipulation of incubation conditions, variation of liposome charge, receptor mediation, and magnetic enhancement. (See, e.g., Pan et al. *Int J Pharm.* 358:263 (2008); Sarbolouki, M. N.

et al., "Storage stability of stabilized MLV and REV liposomes containing sodium methotrexate (aqueous & lyophilized)," *J Pharm Sci Techno.* 52(10):23-27 (1998); Elorza, B., et al., "Comparison of particle size and encapsulation parameters of three liposomal preparations," *J Microencapsul.* 10(2):237-248 (1993); Mykhaylyk, O. et al., "Liposomal Magnetofection," *Methods Mol Bio.* 605:487-525 (2010); all publications incorporated herein by reference in its entirety for all purposes).

Erythrocyte-mediated transfer is similar to liposome fusion and has been shown to have high efficiency and efficacy across all cell types tested (Microinjection and Organelle Transplantation Techniques, Celis et al. Eds.; Academic Press: New York (1986), incorporated by reference in its entirety for all purposes). Typically erythrocytes are loaded by osmotic shock methods or electroporation methods (Schoen, P. et al., Gene transfer mediated by fusion protein hemagglutinin reconstituted in cationic lipid vesicles," *Gene Ther.* 6:823-832 (1999); Li, L. H. et al., "Electrofusion between heterogeneous-sized mammalian cells in a pellet: potential applications in drug delivery and hybridoma formation," *Biophys J.* 71:479-486 (1996); Carruthers, A. et al., "A rapid method of reconstituting human erythrocyte sugar transport proteins," *Biochem.* 23:2712-2718 (1984); each publication is incorporated herein by reference in its entirety for all purposes). Alternatively, erythrocytes may be loaded indirectly by loading hematopoietic progenitors with single-celled organisms and inducing them to differentiate and expand into erythrocytes containing single-celled organisms.

Electroporation is a commonly used, inexpensive method to deliver factors to cells. (Potrykus, I., "Gene transfer methods for plants and cell cultures," *Ciba Found Symp.* 154:198-208, discussion 208-12 (1990); Wolbank, S. et al., "Labeling of human adipose-derived stem cells for non-invasive in vivo cell tracking," *Cell Tissue Bank* 8:163-177 (2007); each publication incorporated herein by reference in its entirety for all purposes).

In another embodiment, a eukaryotic cell that naturally endocytoses bacteria (e.g., Chinese hamster ovary (CHO)) is used. In one embodiment, the modified single-celled bacteria are added to the CHO culture directly. CHO cells are cultured by standard procedures, for example in Ham's F-12 media with 10% fetal calf serum media, prior to infection with the MTB. Post infection, the media is augmented with additional iron (40 to 80 µM) as either ferric malate or $FeCl_3$. Numerous other cell types internalize bacteria by endocytosis or more specifically phagocytosis; endosymbionts or parasites have their own methods for cellular entry and these natural processes can be exploited for internalization of the artificial endosymbionts resulting in the generation of so-called symbiosomes. In another embodiment, symbiosomes from one cell can be transplanted to another cell type (i.e., one incapable of endocytosis of artificial endosymbionts) using microinjection, organelle transplantation, and chimera techniques. These host cells are cultured in typical media and with the techniques for the specific cell type.

In one embodiment, a single-celled organism is introduced to the host cell by a liposome mediated process. Mitochondria and chloroplasts, which are larger than MTB, have been efficiently introduced into eukaryotic cells when encapsulated into liposomes (Bonnett, H. T. *Planta* 131:229 (1976); Giles, K. et al., "Liposome-mediated uptake of chloroplasts by plant protoplasts," *In Vitro Cellular & Developmental Biology—Plant* 16(7):581-584 (1980); each publication incorporated herein by reference in its entirety for all purposes). Numerous liposome fusion protocols and agents are available and can be used by the skilled artisan without undue experimentation (see, e.g., Ben-Haim, N. et al., "Cell-specific integration of artificial organelles based on functionalized polymer vesicles," *Nano Lett.* 8(5):1368-1373 (2008); Lian, W. et al., "Intracellular delivery can be achieved by bombarding cells or tissues with accelerated molecules or bacteria without the need for carrier particles," *Exp Cell Res.* 313(1):53-64 (2007); Heng, B. C. et al., "Immunoliposome-mediated delivery of neomycin phosphotransferase for the lineage-specific selection of differentiated/committed stem cell progenies: Potential advantages over transfection with marker genes, fluorescence-activated and magnetic affinity cell-sorting," *Med Hypotheses* 65(2): 334-336 (2005); Potrykus, *Ciba Found Symp,* 1(54):198 (1990); each publications incorporated herein by reference in its entirety for all purposes).

Methods of Use of Eukaryotic Cells Comprising Single-Celled Organisms

In another aspect, the invention provides methods of using phenotypes introduced into eukaryotic cells by single-celled organisms of the invention. In some embodiments, the phenotype used is a heritable functionality not otherwise present in the eukaryotic cells. In some embodiments, eukaryotic cells with a magnetic phenotype are magnetically manipulated.

In some embodiments, eukaryotic cells of the invention with magnetic phenotypes can be detected and monitored using magnetic detection or imaging techniques such as magnetic resonance imaging (MRI), magnetic particle imaging (MPI), magnetic relaxation switching (MRS), magnetic resonance, superconducting quantum interference (SQUID), magnetometers, nuclear magnetic resonance (NMR), Mossbauer spectrometers, electron paramagnetic resonance (EPR), and magnetic circular dichroism. MRI is a widely used clinical diagnostic tool because it is non-invasive, allows views into optically opaque subjects (including mice, humans, and other mammals), and provides contrast among soft tissues at reasonably high spatial resolution, compared to non-magnetic imaging (such as optical probes) which tend to have low special resolution and to be limited in penetration depth. MPI is a diagnostic method, which like MRI, is non-invasive; however it specifically detects the magnetic fields generated by superparamagnetic iron oxide nanoparticles and results in images with a very low background. Conventional MRI focuses almost exclusively on visualizing anatomy and has no specificity for any particular cell type. The 'probe' used by conventional MRI is the ubiquitous proton $^1H$ in mobile water molecules. Contrast agents can be used for cell-type specificity, but contrast agents dilute or have toxicology issues, and can only be used for short-term studies. Some embodiments of this invention facilitate cell-specific MRI, MPI or other magnetic detection imaging in living subjects for longer-term studies.

In some embodiments, eukaryotic cells of the invention with magnetic phenotypes are mammalian cancer cells, including human cancer cell lines, for example human cancer cell line NCI 60; murine cancer cell lines; and canine cancer cell lines. These magnetic cancer cells can be injected into immunocompromised mammals such as mice and can then be monitored with magnetic imaging to track tumor progression over time. In some embodiments, anti-cancer treatments or putative treatments may be provided to the immunocompromised mammal during the period that tumor progression is being tracked in real time. In some embodiments, viability of eukaryotic cells of the invention with magnetic phenotypes is monitored using MM, MPI or other magnetic detection means to assess in vivo cell response to different conditions, including drug treatments.

In some embodiments, eukaryotic cells of the invention with magnetic phenotypes are metastatic cancer cells that are introduced into experimental animals by methods including injection. MM, MPI or other magnetic detection can then be used to monitor the process of metastasis and movement of metastatic cancer cells throughout the experimental animals. In some embodiments magnetic eukaryotic cancer cells of the invention are injected into a tumor bearing mammal, such as a mouse, and MRI, MPI or other magnetic detection is used to track metastatic cell circulation through the mammal.

In some embodiments, eukaryotic cells of the invention with magnetic phenotypes are macrophages and are injected into experimental animals. Magnetic imaging is used to detect any aggregations of macrophages within the animals. Macrophages aggregate to the sites of inflammation, which can be caused by malignant lesions including metastasis.

In some embodiments, eukaryotic cells of the invention with magnetic phenotypes are stem cells or were derived from stem cells, including ES cells, iPS cells, or adult stem cells obtained from mammalian species, including but not limited to, human, mouse, rat, and pig. Stem cells may be introduced into a target organism directly or may be first differentiated in vitro and then introduced into a target organism. The in vivo fate, including localization, growth rates and viability, of the introduced cells can be assayed through magnetic imaging.

In some embodiments, eukaryotic cells of the invention with magnetic phenotypes are therapeutic T-cells. Therapeutic T-cells may be introduced into a target organism directly, and the in vivo fate, including localization, growth rates and viability, of the introduced cells can be assayed through magnetic imaging.

In some embodiments, eukaryotic cells of the invention with magnetic phenotypes are hematopoietic stem or progenitor cells, which are then introduced into a mammal. When hematopoietic stem or progenitor cells are introduced into mammals, these cells will reside in the bone marrow. The behavior of the magnetic hematopoietic stem or progenitor cells, including their localization, proliferation and mobilization into blood stream upon receiving different stimuli, can be monitored through magnetic imaging.

In some embodiments, magnetic artificial endosymbionts divide more slowly than stem cell host cells in which they reside. Over time, stem cells, which generally divide more slowly than more differentiated progenitor cells, will retain magnetic phenotype longer than more differentiated progenitor cells and the two types of cells will become measurably distinct when imaged magnetically. In some embodiments, eukaryotic cells of the invention with magnetic phenotypes are fused to a eukaryotic cell line of a desired cell type, creating chimeric cells. Chimeric cells can be introduced into an animal and tracked by magnetic imaging.

In some embodiments, eukaryotic cells of the invention with magnetic phenotypes are embryonic cells. In some embodiments, the embryonic cells are fertilized animal eggs, such as mouse or rat. In some embodiments, embryos are implanted into female animals and allowed to develop, leading to the production of animals with cells containing single-celled organism throughout their bodies. Magnetic tissues can be harvested from the resulting organisms and magnetic cell lines can be derived from them. In some embodiments, these animals are bred and the magnetic phenotype is inherited maternally. In some embodiments, eukaryotic cells of the invention with magnetic phenotypes are introduced into multi-celled embryos. The cell lineage of the magnetic cell can be tracked by magnetic imaging as the embryo develops. In some embodiments, the artificial endosymbiont is not retained in the adult animal, but by their presence in the early stages of development the immune system of this animal does not recognize artificial endosymbionts or host cells with artificial endosymbionts as foreign.

In some embodiments, eukaryotic cells of the invention with magnetic phenotypes are moved by magnetically attracting the eukaryotic cells. In some embodiments, this movement is achieved using externally generated magnetic fields and field gradients. Various devices have been reported for magnetic targeting, such as those in U.S. Pat. No. 8,159,224 and Riegler J. et al., "Superparamagnetic iron oxide nanoparticle targeting of MSCs in vascular injury," *Biomaterials* 34(8):1987-94 (2013). In some embodiments, eukaryotic cells of the invention with magnetic phenotypes are separated from a heterogeneous population of non-magnetic cells, either in vitro or in vivo (following introduction into an organism) by using a magnet to attract the magnetic cells.

In some embodiments, eukaryotic cells of the invention with magnetic phenotypes are introduced into the bloodstream or other fluids of a target organism. The eukaryotic cells can be directed to an area of interest on the organism and localized there with an aid of a magnet positioned adjacent to this area. In some embodiments, the eukaryotic cells can be stem cells that are directed to and held in an area on a mammal's body where they could have therapeutic effect. In some embodiments, the eukaryotic cells can be immune cells which can be directed to a particular location on a mammal's body, including to a tumor or injury site. In some embodiments, the eukaryotic cells can be loaded with a therapeutic agent that can be released after being magnetically directed to a desired area.

In some embodiments, eukaryotic cells of the invention with magnetic phenotypes are placed in an alternating magnetic field, or alternative magnetic field, referred to as AMF, for a technique called Magnetic Hyperthermia Technique (MHT). AMF and MHT are described in U.S. Publication No. US20120302819 (U.S. application Ser. No. 13/510,416); and in Silva A. C. et al., "Application of hyperthermia induced by superparamagnetic iron oxide nanoparticles in glioma treatment," *Int J Nanomedicine* 6:591-603 (2011); each publication incorporated herein by reference in its entirety for all purposes). Hyperthermia is a therapeutic procedure that promotes the increase of temperature in body tissues in order to change the functionality of the cellular structures. Its activity is based on the fact that a temperature increase can induce cell damage, including cell lysing and cell death. In some embodiments, the eukaryotic cells of the invention are subjected to an alternating magnetic field for 1, 5, 10, 20, 30, 40, 50 or 60 minutes. In some embodiments, magnetic field frequencies of an applied AMF lie between 50 kHz and 1 MHz. In some embodiments, the magnetic field amplitude of an applied AMF remains below 100 mT. In some embodiments, the eukaryotic cells of the invention subjected to MHT are tumor cells, which are less resistant to sudden increases in temperature than the normal surrounding cells. In some embodiments, the eukaryotic cells of the invention are tumor cells or are next to tumor cells and are subjected to an alternating magnetic field until the internal temperature of the tumor reached between 43° C. and 47° C.

In some embodiments, eukaryotic cells of the invention with magnetic phenotypes are placed in a spinning magnetic field, resulting in rotation of the single-celled organisms inside the cells and cell damage, including cell death. In some embodiments, eukaryotic cells of the invention with magnetic phenotypes in a heterogeneous population of non-magnetic cells are selectively damaged by subjecting the entire cell population to an alternating magnetic field or to a spinning magnetic field. In some embodiments, eukaryotic cells of the invention with magnetic phenotypes in a heterogeneous population of non-magnetic cells are placed in an alternating magnetic field or a spinning magnetic field, resulting in damage to both the eukaryotic cells of the invention and the non-magnetic cells located near the cells of the invention. In some embodiments, eukaryotic cells of the invention with magnetic phenotypes are introduced into an animal and are targeted to a location within the animal by magnetic manipulation or other forms of cell targeting known in the art. The location within the animal can then be subjected to an alternating magnetic field or a spinning magnetic field, resulting in the damage to cells surrounding the magnetic cells. In some embodiments, eukaryotic cells of the invention with magnetic phenotypes are introduced into an animal and are targeted to a tumor site within the animal by magnetic manipulation or other forms of cell targeting known in the art. The tumor can then be subjected to an alternating magnetic field or a spinning magnetic field, resulting in the damage to tumor cells surrounding the magnetic cells. In some embodiments, eukaryotic cells of the invention with magnetic phenotypes are stem cells, including ES cells, iPS cells, or adult stem cells obtained from mammalian species including but not limited to human, mouse, rat, and pig. Stem cells may be introduced into a target organism directly or may be first differentiated in vitro and then introduced into a target organism. Following introduction, the animal can be subjected to an alternating magnetic field or a spinning magnetic field, resulting in the death of introduced stem cells and resulting lineages of these stem cells. The in vivo fate, including localization, growth rates and viability, of the introduced cells can be assayed through magnetic imaging.

Multimodal Detection

In another aspect, the present invention is directed to eukaryotic cells engineered with a single-celled organism, such as an artificial endosymbiont. The singled-celled organism may impart at least one desired phenotype into the eukaryotic cell. In some embodiments, the single-celled organism may secrete to and/or transport from the host cell polypeptide(s), nucleic acid(s), lipid(s), carbohydrate(s), amino acid(s), or other factor(s). This communication between the single celled organism and the host cell may result in the desired phenotype or phenotypes for the eukaryotic cell. Such a desired phenotype or desired phenotypes may allow for multimodal detection or observation of the eukaryotic cells. Thus, in some embodiments, the single cell organism can be used as multimodal probes for multimodal detection or observation of the eukaryotic cells.

In some embodiments, the multimodal probe comprises a magnetic bacteria expressing one or more reporters for multimodal detection. In some embodiments, the magnetic bacteria comprise a magnetotactic bacteria expressing one or more reporters for multimodal detection. In some embodiments, for use as a multimodal probe, a heterologous gene encoding the reporter protein is introduced into the magnetic bacteria such that the genetically modified magnetic bacteria express the reporter. In some embodiments, the magnetic bacteria are engineered to express a single reporter. In some embodiments, different magnetic bacteria, each expressing a different reporter, is introduced into a eukaryotic cell for multimodal detection. In some embodiments, the magnetic bacteria is engineered to express two or more reporter products, for example by using a single vector construct encoding two or more reporters. In some embodiments, the reporters comprise heterologous reporters and are expressed in a form functional for detection. The expression of reporter genes provides for additional imaging modalities, in addition to the magnetic phenotype of the magnetic bacteria.

For example, the present disclosure shows effective reporter gene expression for two modalities using the magnetotactic bacterial strain *Magnetospirillum magneticum* (AMB-1). In some embodiments for expressing a reporter gene, a plasmid containing a reporter gene and a suitable resistance gene (e.g., one which confers antibiotic resistance) can be introduced into *Escherichia coli* cells, mating the *E. coli* cells with the target magnetotactic bacterial cells, and then performing selection on the magnetotactic bacteria. An appropriate assay can then be performed on the transformed magnetotactic bacteria to confirm the presence and positive expression of the reporter. In some embodiments, when selecting a reporter gene for incorporation, care is taken to ensure that it can still be expressed in a functional form using prokaryotic transcriptional and translational machinery. These modified bacteria have a magnetic phenotype and the phenotype of the reporter gene, which allow for multimodal detection of eukaryotic cells carrying the genetically modified magnetotactic bacteria. Introduction and expression of additional reporter genes, where each reporter gene is detectable using a different imaging modality, provides for additional imaging capabilities.

In some embodiments, the magnetosomes of the genetically modified magnetic bacteria can be detected using MM systems, magnetic particle imaging (MPI) systems, magnetic relaxation switching (MRS) systems, magnetic resonance spectrometers, superconducting quantum interference devices (SQUID), magnetometers, nuclear magnetic resonance (NMR) systems, Mossbauer spectrometers, electron paramagnetic resonance (EPR) systems, and magnetic circular dichroism systems. The product of the reporter gene can be detected by any appropriate detection method and apparatus, depending on the type of reporter product expressed from the reporter gene. By way of example, an exemplary reporter gene encodes a light producing protein (e.g., luciferase or eGFP), and this phenotype can be detected using optical imaging, which can be performed either non-invasively (for BLI and FLI) or with some degree of invasiveness, for example, intravital microscopy and fluorescence laparoscopy (see. e.g., Gahlen, J. et al., "Laparoscopic fluorescence diagnosis for intraabdominal fluorescence targeting of peritoneal carcinosis," *Ann Surg*. 235: 252-260 (2002), incorporated herein by reference in its entirety for all purposes). In the descriptions herein, expression of a reporter is meant to include expression of the corresponding reporter gene resulting in expression of the encoded reporter or reporter molecule.

In some embodiments, the multimodal probe comprises a magnetic (e.g., magnetotactic) bacterial cell expressing one or more reporters selected from a Positron Emission Tomography (PET) reporter, a Single Photon Emission Computed Tomography (SPECT) reporter, an X-Ray reporter, a photoacoustic reporter, and an ultrasound reporter.

In some embodiments, the multimodal probe further expresses, in addition to the above reporters, a fluorescent reporter or a bioluminescent reporter. In some embodiments, the multimodal probe further expresses, in addition to the above reporters, a fluorescent and a bioluminescent reporter.

In some embodiments, the multimodal probe expresses at least a Positron Emission Tomography (PET) reporter. Various PET reporters can be expressed and used in the multimodal probes. In some embodiments, the PET reporter comprises a thymidine kinase. In some embodiments, the thymidine kinase is selected from a Herpes Simplex Virus thymidine kinase, Varicella-Zoster Virus thymidine kinase, human mitochondrial thymidine kinase or active variants thereof (see, e.g., Campbell et al., *J Biol Chem.* 287(1):446-54 (2012)). PET detection of thymidine kinase is generally achieved by using a PET-specific reporter probe. Exemplary PET reporter probe for HSV thymidine kinase includes [$^{18}$F]9-(4-[18F]-fluoro-3-hydroxymethylbutyl)-guanine, a fluorine-18-labelled penciclovir analogue, which when phosphorylated by thymidine kinase (TK) becomes retained intracellularly. Another thymidine kinase reporter probe is 5-(76) Br-bromo-2'-fluoro-2'-deoxyuridine. In some embodiments, a thymidine kinase reporter probe that is preferentially acted on by the heterologous thymidine kinase as compared to any endogenous thymidine kinase is used.

Other PET reporters that can be used in the multimodal probe include, among others, dopamine D2 (D2R) receptor, sodium iodide transporter (NIS), dexoycytidine kinase, somatostatin receptor subtype 2, norepinephrine transporter (NET), cannaboid receptor, glucose transporter (Glut1), tyrosinase, and active variants thereof. The relevant reporter probes for each of the PET reporters are well known to the skilled artisan. An exemplary reporter probe for dopamine D2 (D2R) receptor is 3-(2'-[$^{18}$F]fluoroethyl)spiperone (FESP) (MacLaren et al., *Gene Ther.* 6(5):785-91 (1999)). An exemplary reporter probe for the sodium iodide transporter is $^{124}$I, which is retained in cells following transport by the transporter. An exemplary reporter probe for deoxycytidine kinase is 2'-deoxy-2'-$^{18}$F-5-ethyl-1-β-d-arabinofuranosyluracil ($^{18}$F-FEAU). An exemplary reporter probe for somatostatin receptor subtype 2 is $^{111}$In-, $^{99m/94m}$Tc-, $^{90}$Y-, or $^{177}$Lu-labeled octreotide analogues, for example $^{90}$Y-, or $^{177}$Lu-labeled DOTATOC (Zhang et al., *J Nucl Med.* 50(suppl 2):323 (2009)); $^{68}$Ga-DOTATATE; and $^{111}$In-DOTABASS (see. e.g., Brader et al., *J Nucl Med.* 54(2):167-172 (2013), incorporated herein by reference). An exemplary reporter probe for norepinephrine transporter is $^{11}$C-m-hydroxyephedrine (Buursma et al., *J Nucl Med.* 46:2068-2075 (2005)). An exemplary reporter probe for the cannaboid receptor is $^{11}$C-labeled CB$_2$ ligand, $^{11}$C-GW405833 (Vandeputte et al., *J Nucl Med.* 52(7):1102-1109 (2011)). An exemplary reporter probe for the glucose transporter is [$^{18}$F]fluoro-2-deoxy-d-glucose (Herschman, H. R., *Crit Rev Oncology/Hematology* 51:191-204 (2004)). An exemplary reporter probe for tyrosinase is N-(2-(diethylamino)ethyl)-$^{18}$F-5-fluoropicolinamide (Qin et al., *Sci Rep.* 3:1490 (2013)). Other reporter probes are described in the art, for example, in Yaghoubi et al., *Theranostics* 2(4):374-391 (2012), incorporated herein by reference.

In some embodiments, the multimodal probe expresses at least a Single Photon Emission Computed Tomography (SPECT) reporter. Exemplary SPECT reporters include sodium iodide transporter, dopamine D2 (D2R) receptor, and active variants thereof. In some embodiments, the SPECT reporter comprises a modified haloalkane dehalogenase capable of covalently bonding a SPECT detectable chloroalkane substrate (see, e.g., Hong et al., *Am J Transl Res.* 5(3):291-302 (2013), incorporated herein by reference).

In some embodiments, the multimodal probe expresses at least a photoacoustic reporter. Exemplary photoacoustic reporters include, among others, tyrosinase and β-galactosidase (see, e.g., Krumholz et al., *J Biomed Optics.* 16(8):1-3 (2011)). Reporter probes for tyrosinase have been described above. An exemplary reporter probe for β-galactosidase is 5-bromo-4-chloro-3-indolyl-β-D-galactoside (X-gal) (Li et al., *J Biomed Opt.* 12(2):020504 (2007)).

In some embodiments, the multimodal probe expresses at least an X-ray reporter. Exemplary X-ray reporter includes, among others, somatostatin receptor 2, or other types of receptor based binding agents. The reporter probe can have a radiopaque label moiety that is bound to the reporter probe and imaged, for example, by X-ray or computer tomography. Exemplary radiopaque label is iodine, particularly a polyiodinated chemical group (see, e.g., U.S. Pat. No. 5,141,739), and paramagnetic labels (e.g., gadolinium), which can be attached to the reporter probe by conventional means.

In some embodiments, the multimodal probe expresses at least an ultrasound reporter. Exemplary ultrasound reporter includes, among others, a binding agent that is capable of binding an ultrasound contrast agent, for example, microbubble contrast agent. For example, the binding agent can comprise an antibody expressed in the magnetotactic bacteria and directed specifically against a peptide, where the peptide is bound to microbubble contrast agents (see, e.g., Kiessling et al., *J Nucl. Med.* 53:345-348 (2012)).

In the embodiments herein where the reporter is a fluorescent reporter, any number of fluorescent reporters can be used. These include, for example, green fluorescent protein from *Aequorea victoria* or *Renilla reniformis*, and active variants thereof (e.g., blue fluorescent protein, yellow fluorescent protein, cyan fluorescent protein, etc.); fluorescent proteins from Hydroid jellyfishes, Copepod, Ctenophora, Anthrozoas, and Entacmaea quadricolor, and active variants thereof; and phycobiliproteins and active variants thereof.

In some embodiments herein where the reporter is a bioluminescent reporter, any number of bioluminescent proteins can be used as the reporter. These include, by way of example and not limitation, aequorin (and other Ca$^{+2}$ regulated photoproteins), luciferase based on luciferin substrate, luciferase based on Coelenterazine substrate (e.g., *Renilla, Gaussia,* and *Metridina*), and luciferase from Cypridina, and active variants thereof.

In some embodiments, the multimodal probe expresses at least two or more reporters, at least three or more reporters, at least four or more reporters, or at least five or more reporters selected from a fluorescent reporter, a bioluminescent reporter, a PET reporter, a SPECT reporter, an X-ray reporter, a photoacoustic reporter, and ultrasound reporter.

In some embodiments, the multimodal probe expresses at least two reporters selected from a fluorescent reporter, a bioluminescent reporter, a PET reporter, a SPECT reporter, an X-ray reporter, a photoacoustic reporter, and ultrasound reporter.

In some embodiments, the multimodal probe expresses at least three reporters selected from a fluorescent reporter, a bioluminescent reporter, a PET reporter, a SPECT reporter, an X-ray reporter, a photoacoustic reporter, and ultrasound reporter.

In some embodiments, the reporter gene for the multimodal probe encodes a reporter that is detectable by multiple imaging modalities, for example tyrosinase which has been shown to yield photoacoustic imaging (PAI), MRI and PET (with a suitable radiotracer) signals (see, e.g., Qin, C. et al., "Tyrosinase as a multifunctional reporter gene for photoacoustic/MRI/PET triple modality molecular imaging," *Scientific Rep.* 3:1490 (2013), incorporated herein by reference in its entirety for all purposes). Alternatively, the reporter gene can be a fusion protein comprising two or more reporters linked together (e.g., a luciferase-GFP-thymidine kinase triple fusion reporter). (Ray P. et al., "Imaging tri-fusion multimodality reported gene expression in living subjects," *Cancer Res.* 64:1323-1330 (2004), incorporated herein by reference in its entirety for all purposes). In some embodiments, each of the reporters comprises different reporters, each reporter being detectable by a different imaging modality.

In some embodiments, the gene expressing the heterologous reporter can be extrachromosomal, for example, as part of self-replicating plasmids, cosmids, or bacmids. In some embodiments, the genes expressing the reporter can be integrated into the bacterial chromosome, for example through homologous recombination, or integration mediated by recombinases, such a Cre-loxP, Dre-rox, yeast flippase (FLP), and attTn7 based integration (Choi et al., *Appl Environ Microbiol.* 72(1):753-758 (2008)). In some embodiments, the reporter gene is constructed to express the functional reporter without fusions to other proteins. In some embodiments, the reporter gene is constructed to express the functional reporter as fusions, i.e., a fusion protein, for example to other heterologous proteins or proteins of the magnetotactic bacteria.

In some embodiments, genetically modified magnetic bacteria are introduced to eukaryotic cells for multimodal detection. Once inside the eukaryotic cell, the genetically modified magnetic bacteria have the capacity to self-replicate, thus maintaining their levels even after a cell division event, which makes them a powerful tool for long term cell tracking and other imaging capabilities. The magnetotactic bacteria's magnetite-based iron cores are capable of generating a powerful in vivo MRI signal. Moreover, the genetically modified magnetic bacteria can have additional functionality prior to incorporation into eukaryotic cells, for example by addition of reporter genes to permit imaging of the genetically modified magnetic bacteria and cells labeled with the genetically modified magnetic bacteria using multimodal imaging. The eukaryotic cell comprising the multimodal probes can comprise any of the cells described above, including plant cells and animal cells. In some embodiments, the eukaryotic cell comprising the multimodal probes is a mammalian cell. In some embodiments, the mammalian cell can comprise a cell of a mouse (murine), rat, rabbit, hamster, human, porcine, bovine, or canine. In some embodiments, the mammalian cell is a cancer cell or stem cell, including specific cancer cells, stem cells, and embryonic cells described in the present disclosure.

Accordingly, in some embodiments, a eukaryotic cell can comprise membrane-enclosed magnetosomes and at least one expressed reporter. In some embodiments, the eukaryotic cell can comprise a magnetic bacteria, where the bacteria are capable of expressing or expresses one or more reporters. In some embodiments, the eukaryotic cell can comprise a magnetotactic bacteria, where the bacteria are capable of expressing or expresses one or more reporters. In some embodiments, the reporter is selected from: a fluorescent reporter, a bioluminescent reporter, a Positron Emission Tomography (PET) reporter, Single Photon Emission Computed Tomography (SPECT) reporter, X-Ray reporter, photoacoustic reporter, and an ultrasound reporter, as described herein.

In some embodiments, the eukaryotic cell comprises a magnetic bacteria, where the bacteria express at least two or more reporters. In some embodiments, the two or more reporters are selected from a fluorescent reporter, a bioluminescence reporter, a Positron Emission Tomography (PET) reporter, Single Photon Emission Computed Tomography (SPECT) reporter, X-Ray reporter, photoacoustic reporter, and an ultrasound reporter.

In some embodiments, the eukaryotic cell comprises a magnetic bacteria, where the bacteria expresses at least three or more reporters. In some embodiments, the three or more reporters are selected from a fluorescent reporter, a bioluminescence reporter, a Positron Emission Tomography (PET) reporter, Single Photon Emission Computed Tomography (SPECT) reporter, X-Ray reporter, photoacoustic reporter, and an ultrasound reporter.

In some embodiments, the eukaryotic cell comprises a magnetic bacteria, where the bacteria expresses at least one reporter selected from: a Positron Emission Tomography (PET) reporter, Single Photon Emission Computed Tomography (SPECT) reporter, X-Ray reporter, photoacoustic reporter, and an ultrasound reporter. In some embodiments, the magnetotactic bacteria expressing one or more of the foregoing reporters, can also express a fluorescent reporter, a bioluminescent reporter, or both a fluorescent and bioluminescent reporter.

In some embodiments, the eukaryotic cell comprises a single-celled organism, where the eukaryotic cell is detectable by multiple imaging modalities. The imaging modalities can be selected from ultrasound imaging, computed tomography imaging, optical imaging, magnetic resonance imaging, optical coherence tomography imaging, radiography imaging, nuclear medical imaging, positron emission tomography imaging, tomography imaging, photo acoustic tomography imaging, x-ray imaging, thermal imaging, fluoroscopy imaging, bioluminescent imaging, and fluorescent imaging, magnetic particle imaging, and magnetic resonance spectroscopy. In some embodiments, the eukaryotic cell is detectable by at least two or more, three or more, four or more, or five or more of the foregoing imaging modalities.

In some embodiments, the eukaryotic cell is detectable by multiple modalities, where at least one of the modalities is magnetic resonance imaging. That is, the eukaryotic cell is detectable by a first modality, where the first modality is magnetic resonance imaging. In some embodiments, the eukaryotic cell is detectable by a second modality selected from ultrasound imaging, computed tomography imaging, optical imaging, optical coherence tomography imaging, radiography imaging, nuclear medical imaging, positron emission tomography imaging, single-photon emission computerized tomography, tomography imaging, photoacoustic tomography imaging, X-ray imaging, thermal imaging, fluoroscopy imaging, bioluminescent imaging, and fluorescent imaging, magnetic particle imaging, and magnetic resonance spectroscopy.

In some embodiments, the eukaryotic cell is detectable by multiple modalities, where at least one of the modalities is magnetic particle imaging. In other words, the eukaryotic cell is detectable by a first modality, where the first modality is magnetic particle imaging. In some embodiments, the eukaryotic cell is detectable by a second modality selected from ultrasound imaging, computed tomography imaging, optical imaging, optical coherence tomography imaging, radiography imaging, nuclear medical imaging, positron emission tomography imaging, single-photon emission computerized tomography, tomography imaging, photoacoustic tomography imaging, X-ray imaging, thermal imaging, fluoroscopy imaging, bioluminescent imaging, fluorescent imaging, and magnetic resonance spectroscopy.

In some embodiments, where the eukaryotic cell is detectable by magnetic resonance imaging or magnetic particle imaging, the second modality is fluorescent imaging. In some embodiments, the second modality is bioluminescent imaging. In some embodiments, the second modality is PET imaging. In some embodiments, the second modality is photoacoustic imaging. In some embodiments, the second modality is X-ray imaging. In some embodiments, the second modality is ultrasound imaging. In some embodiments, the eukaryotic cell is detectable by a third modality, a fourth modality, fifth modality, sixth modality or more modalities, where each modality is different.

While use of magnetic bacteria expressing one or more reporter genes provides flexibility, in some embodiments, the eukaryotic cell itself can also express one or more reporters. In particular, the eukaryotic cell comprises a magnetic bacteria, where the eukaryotic cell expresses one or more reporters. Any of the reporters described herein can be expressed in the eukaryotic cell comprising the magnetic bacteria. In some embodiments, the eukaryotic cell can express a reporter selected from a fluorescent reporter, a bioluminescent reporter, a Positron Emission Tomography (PET) reporter, Single Photon Emission Computed Tomography (SPECT) reporter, X-Ray reporter, photoacoustic reporter, and an ultrasound reporter.

In some embodiments of the eukaryotic cell comprising a magnetotactic bacteria, the eukaryotic cell can express one or more reporters, and the magnetotactic bacteria can express one or more reporters. In some embodiments, the set of reporters expressed by the eukaryotic cell is different from the set of reporters expressed by the magnetic bacteria. In some embodiments, expression of different reporters by the eukaryotic cell and the magnetotactic bacteria provides a method of distinguishing the eukaryotic cell from the eukaryotic cell containing the magnetotactic bacteria.

In the embodiments herein, the multimodal probes can be used to image any cell, tissue, or organism containing the multimodal probe. In particular, the multimodal probes can be introduced into eukaryotic cells, e.g., as artificial endosymbionts, and the eukaryotic cell imaged by any of the methods described herein. The eukaryotic cell comprising the multimodal probes can be imaged in isolation or as part of a tissue or organism.

Accordingly, in some embodiments, the compositions can be used in a multimodal imaging method comprising: (a) magnetically imaging a magnetotactic bacterium expressing one or more heterologous reporters, and (b) imaging the reporter using a non-magnetic imaging modality.

In some embodiments, the multimodal imaging method can comprise: (a) magnetically imaging a eukaryotic cell comprising a magnetotactic bacterium, and (b) imaging the eukaryotic cell by imaging one or more expressed reporters using at least one non-magnetic imaging modality. Any of the reporters described in the present disclosure can be used in the imaging methods. These include a reporter selected from a fluorescent reporter, a bioluminescent reporter, a Positron Emission Tomography (PET) reporter, Single Photon Emission Computed Tomography (SPECT) reporter, X-Ray reporter, photoacoustic reporter, and an ultrasound reporter.

In some embodiments, the eukaryotic cell can be multimodally detected using magnetic imaging, for example magnetic resonance imaging or magnetic particle imaging, and an appropriate optical imaging technique. In some embodiments, an optical imaging technique is based on expression of a fluorescent reporter, for example green fluorescent protein or active variants thereof.

In some embodiments, the eukaryotic cell can be multimodally detected using magnetic imaging, for example magnetic resonance imaging or magnetic particle imaging, and an appropriate PET imaging technique. In some embodiments, the PET imaging technique is based on expression of a PET reporter, for example thymidine kinase or cytidine kinase. In this embodiment, the eukaryotic cell can be multimodally detected using MM and PET imaging.

In some embodiments, the eukaryotic cell can be multimodally detected using magnetic imaging, for example magnetic resonance imaging or magnetic particle imaging, and an appropriate photoacoustic imaging technique. In some embodiments, the photoacoustic imaging technique is based on expression of a photoacoustic reporter, for example tyrosinase or β-galactosidase. In this embodiment, the eukaryotic cell can be multimodally detected using MM and photoacoustic imaging.

As discussed herein, the multimodal probes and imaging techniques can be used to image eukaryotic cells, including eukaryotic cells that are part of tissues or multicellular organisms. In some embodiments, a multimodal imaging method for imaging a tissue or multicellular organism, comprises: (a) imaging a eukaryotic cell comprising a magnetotactic bacterium by a first imaging modality, wherein the eukaryotic cell is a component of a tissue or multicellular organism and the magnetotactic bacterium expresses one or more heterologous reporters, and wherein the first imaging modality is a magnetic modality; (b) optionally imaging the eukaryotic cell by imaging one or more of the expressed reporters using a second imaging modality, wherein the second modality is a non-magnetic modality; and (c) imaging the tissue or organism by a third imaging modality. In some embodiments, the eukaryotic cell is imaged according to step (b). As will be apparent to the skilled artisan, in some embodiments, the second imaging modality encompasses one or more imaging methods, i.e., modalities, in view of the multiple reporters that can be expressed in the magnetotactic bacteria.

In some embodiments of the method of imaging a tissue or multicellular organism, the first imaging modality is magnetic particle imaging or magnetic resonance imaging. In some embodiments, the second imaging modality comprises a non-magnetic imaging modality selected from ultrasound imaging, computed tomography imaging, optical imaging, optical coherence tomography imaging, radiography imaging, nuclear medical imaging, positron emission tomography imaging, tomography imaging, photoacoustic tomography imaging, x-ray imaging, thermal imaging, fluoroscopy imaging, bioluminescent imaging, and fluorescent imaging.

In some embodiments of the method of imaging a tissue or multicellular organism, the third imaging modality is different from the first imaging modality. In some embodiments, the third imaging modality is a non-magnetic imaging modality. In some embodiments, the third imaging modality is selected from ultrasound imaging, computed tomography imaging, optical imaging, optical coherence tomography imaging, radiography imaging, nuclear medical imaging, positron emission tomography imaging, tomography imaging, photoacoustic tomography imaging, X-ray imaging, thermal imaging, fluoroscopy imaging, bioluminescent imaging, and fluorescent imaging.

In some embodiments, multimodality is used for non-invasive in vivo imaging. Generally, imaging modalities can be described as either anatomic or functional in terms of the information they provide. Anatomic modalities include X-ray Computed Tomography (CT), Magnetic Resonance Imaging (MRI) and Ultrasound (US), and these describe various aspects of the subject anatomy (e.g., variations in material density for CT, proton environments for MM, and acoustic reflectivity for US). Functional modalities include Positron Emission Tomography (PET), Single Photon Emission Computed Tomography (SPECT), Fluorescence Imaging (FLI) and Bioluminescence Imaging (BLI), certain types of MRI (such as Diffusion Weighted (DW) or Dynamic Contrast Enhanced (DCE)), Magnetic Particle Imaging (MPI), Photoacoustic Imaging (PAI), contrast-enhanced Ultrasound (ceUS), Raman Imaging (RI), contrast-enhanced CT (ceCT) and X-Ray Fluorescence CT (XFCT) (Kuang, Y. et al., "First demonstration of multiplexed X-ray fluorescence computed tomography (XFCT) imaging," *IEEE Trans Med Imaging* 32:262-267 (2012), which is incorporated by reference in its entirety for all purposes), describe specific biological processes occurring within host cells (including the single-celled organism) (James, M. L. et al., "A molecular imaging primer: modalities, imaging agents, and applications," *Physiol Rev.* 92:897-965 (2012); Molecular Imaging: Principles and Practice, Eds. Weissleder, R., Ross, B. D., Rehemtulla A. and Gambhir, S. S., People's Medical Publishing House, USA, (2010); each publication incorporated herein by reference in their entirety for all purposes). This occurs because the signal being measured is produced by a specific probe molecule which can be a chemical (a contrast agent) or protein (a reporter protein). Contrast agents are exogenous and are administered to the subject before the scan, whilst reporter proteins are produced by reporter genes which are genetically encoded into host cells or the single-celled organism.

In some embodiments, multimodal imaging of the present disclosure is used to track eukaryotic cells in vivo. In order to track cells for multiple generations of eukaryotic cells, the probe needs to be able to maintain a detectable concentration as the eukaryotic cell divides. Contrast agent methods, which include the nanoparticle approach described above, generally do not satisfy this requirement as they rapidly dilute to undetectable levels after a few rounds of cell division. Reporter genes expressing detectable reporters are able to maintain persistent detectable levels, but require extensive genetic engineering of the eukaryotic cell. In addition, there exist few useful reporter gene options for long term cell imaging with MM. Researchers have experimented with MM reporter genes using the ferritin heavy chain gene (see, e.g., Cohen, B. et al., "Ferritin as an endogenous MM reporter for noninvasive imaging of gene expression in C6 glioma tumors," *Neoplasia* 7:109-117 (2005), incorporated herein by reference in its entirety for all purposes), and with genes such as MagA derived from magnetotactic bacteria (Goldhawk D. E. et al., "Magnetic resonance imaging of cells overexpressing MagA, an endogenous contrast agent for live cell imaging," *Mol Imaging* 8:129-139 (2009); Zurkiya, O. et al., "MagA is sufficient for producing magnetic nanoparticles in mammalian cells, making it an MM reporter," *Magnet Reson Med.* 59:1225-1231 (2008), each of which are incorporated herein by reference in their entirety for all purposes), but the contrast obtainable from this approach is typically weak, and provides poor detectability. An advantage of multimodal probes described herein, e.g., magnetic bacteria expressing one or more reporters, is that the genetically modified magnetic bacteria can be readily introduced into a eukaryotic cell, and the magnetic bacteria in the eukaryotic cells are heritable to daughter cells such that reporter levels can be maintained.

In some embodiments for multimodal imaging, the multimodal probe or the eukaryotic cell comprising the multimodal probe is contacted with an appropriate reporter probe under suitable conditions to detect presence of the corresponding expressed reporter, for example a PET, SPECT, photoacoustic, X-ray, or ultrasound reporter. Where the tracking of cells or imaging is in a tissue or in vivo in an animal, the tissue or the animal can be administered the appropriate reporter probe to detect and/or image expression of the corresponding reporter. Exemplary reporter probes for corresponding reporters and the imaging methods have been described above. The reporter probes can be administered to the tissue or animal host by various routes. In some embodiments, suitable reporter probes can be administered orally or parenterally. Parenteral administration in this respect includes administration by intravenous, intramuscular, subcutaneous, intraocular, intrasynovial, transepithelial, including transdermal, ophthalmic, sublingual and buccal; topically including ophthalmic, dermal, ocular, rectal and nasal inhalation via insufflation, aerosol and rectal systemic. The reporter probes are administered in a variety of forms, including formulations with pharmaceutically acceptable excipients or carriers. The pharmaceutically acceptable excipients and carriers are substantially non-toxic and of pharmaceutically acceptable purity. In some embodiments, the forms suitable for injection can include, for example, sterile aqueous solutions or dispersions and sterile powders for the extemporaneous preparation of sterile injectable solutions or dispersions. In some embodiments, the reporter probes can be prepared for oral administration, for example as orally administered solutions, tablets, capsules or powders.

In some embodiments, as discussed above, multimodal imaging can be performed in several ways. The first is to image a subject or target using different imaging modalities, thus acquiring multiple image types which are then aligned to enable a comparison of the different images across each imaged part of the subject. In some embodiments, an exemplary combination is an anatomic scan (e.g., CT) and a functional scan (e.g., PET), as this allows the functional data to be placed within an anatomic context. In some embodiments, multimodal scanners can be used for the acquisition of two or more image types at the same time. Two commonly used examples are combined PET/CT scanners, optical imagers which permit the acquisition of FLI, BLI and widefield images, and US scanners which also perform Photo-Acoustic Imaging (PAI). It is to be understood that acquisition of many different combinations of image types are possible.

In some embodiments, multimodal imaging can be done by using a probe which produces an observable signal in two or more imaging modalities. This has the advantage that the imager can use a range of imaging methods to image the probe and permits greater flexibility in designing imaging studies, as the multimodal probe can be used to introduce desired phenotypes into a subject or target, permitting use of desired imaging modalities of the subject or target. To this end, in some embodiments, the multimodal probe can express at least two reporters, for example by use of a double fusion reporter construct expressing two reporter genes, enabling use of at least two imaging modalities. In some embodiments, the multimodal probe can express at least three reporters, for example by use of a triple fusion reporter construct expressing three reporter genes, which enables use of at least three imaging modalities, for example, FLI, BLI and PET to image cells which have been engineered to express it. In some embodiments, the probe can be a single probe which produces an observable signal in two or more imaging modalities. An exemplary probe capable of being imaged with two or more imaging modalities is reporter tysosinase, which can be imaged using PET, MM and photoacoustic imaging techniques. In view of the guidance herein, numerous variations on this approach can be made and are to be explicitly described in the present disclosure.

In some embodiments, multimodal images are collected and include at least two of the following types of images: one or more images corresponding to light emitted from the cell, one or more images corresponding to light transmitted by the cell, and one or more images corresponding to light scattered by the cell. Such multimode imaging can encompass any of the following types of images or combinations: (1) one or more fluorescent images and at least one bright field image; (2) one or more fluorescent images and at least one dark field image; (3) one or more fluorescent images, a bright field image, and a dark field image; and (4) a bright field image. Simultaneous collection of a plurality of different fluorescent images (separated by spectrum) can also be beneficial, as well as simultaneous collection of a plurality of different bright field images (using transmitted light with two different spectral filters). Preferably, the multimode images are collected simultaneously.

In some embodiments, multimodal imaging can compensate for very low signal by combining the low signal with anatomical imaging data that is spatially registered with the low signal from another modality of detection. In some embodiments, different imaging methods (or modalities) allow the visualization of different aspects of the eukaryotic cell and its environment, and combining these multiple modalities allows one to learn more about the eukaryotic cell and its environment.

In some embodiments, the image acquired by any one modality in any of the methods above can be processed in a variety of ways, for example comparing and reconstructing the image data. In some embodiments, one image obtained using one modality can be compared to image obtained using a different modality. In some embodiments, the comparison and/or reconstruction can be carried out by overlaying image acquired from one modality to the image acquired from a different modality. Comparisons and/or reconstructions can be carried out for 2 or more images, 3 or more images, 4 or more images, 5 or more images, or 6 or more images, where each image is acquired using different modalities. In general, the images are in the form of pixel images. For example, in the multimodal imaging method, comprising: (a) magnetically imaging a magnetotactic bacterium expressing one or more heterologous reporters, and (b) imaging the reporter using a non-magnetic modality, the method can further comprise overlaying to each other the image acquired/captured from (a) and the image acquired/captured from (b). In some embodiments, the image in (a) and the image in (b) comprise pixel images. Various methods for image processing, including comparing or reconstructing images obtained by different modalities are described in, for example, U.S. patent publication Nos. 20110262016 and 20130177224.

In addition to the advantage of the heritability of magnetic bacteria in eukaryotic cells, which overcomes the need to construct eukaryotic cells expressing a reporter while maintaining levels of the reporter for detection, use of multimodal imaging based on magnetic bacteria as a multimodal probe allows enhanced imaging of localization and tracking of eukaryotic cells, including imaging of changes in cell dynamics, such as within tissues containing the eukaryotic cells. This added dimension enhances the ability to track cells and tissues containing such cells.

For example, in some embodiments, the multimodal probes can be introduced into cancer cells, and the modified cancer cells introduced into experimental animals, for example to track metastasis and movement of cancer cells in the animal. The cancer cells can also be tracked and imaged following various therapeutic treatments to assess the treatment's effectiveness and examine the dynamics of cancer cell viability and migration before and after treatment.

In some embodiments, the multimodal probes can be introduced into stem cells to track the stem cell's in vivo fate, including localization, growth rate and viability. Where the stem cells are hematopoietic stem or progenitor cells, the stem cells containing the multimodal probes are introduced into a mammal and the behavior of the magnetic hematopoietic stem or progenitor cells, including their localization, proliferation and mobilization into blood stream upon receiving different stimuli, monitored through multimodal imaging. This can be coupled to different types of treatments meant to facilitate stem cell transplantation and homing. Other uses of the multimodal imaging methods will be apparent in view of the guidance provided in the present disclosure.

The inventions disclosed herein will be better understood from the experimental details which follow. However, one skilled in the art will readily appreciate that the specific methods and results discussed are merely illustrative of the inventions as described more fully in the claims which follow thereafter.

EXAMPLES

Example 1: Microinjection of Gfp$^+$AMB-1 into Murine Cells

A. Construction of gfp$^+$AMB-1.

Expression vectors for eGFP, one including a Shine-Dalgarno sequence upstream of the gfp gene and one without a Shine Dalgarno, sequence were cloned into cryptic broad host range vector pBBR1MCS-2 (Kovach, M. E. et al., "Four new derivatives of the broad-host-range cloning vector pBBR1MCS, carrying different antibiotic-resistance cassettes," *Gene* 166, 175-176, (1995), incorporated herein by reference in its entirety for all purposes). AMB-1 (ATCC 700264) was transformed with this construct (see, e.g., Matsunaga, T. et al., "Complete genome sequence of the facultative anaerobic magnetotactic bacterium *Magnetospirillum* sp. strain AMB-1," *DNA Res.* 12, 157-166 (2005); Burgess J. G., et al., "Evolutionary relationships among *Magnetospirillum* strains inferred from phylogenetic analysis of 16S rDNA sequences," *J Bacteriol.* 175:6689-6694 (1993); Matsunaga T, et al., "Gene transfer in magnetic bacteria: transposon mutagenesis and cloning of genomic DNA fragments required for magnetosome synthesis," *J Bacteriol.* 174: 2748-2753 (1992); Kawaguchi R, et al., "Phylogeny and 16s rRNA sequence of *Magnetospirillum* sp. AMB-1, an aerobic magnetic bacterium," *Nucleic Acids Res.* 20:1140 (1992); each publication incorporated herein by reference in its entirety for all purposes).

Transformation was achieved by conjugation using a donor *Escherichia coli* strain (see Goulian, M. et al., "A simple system for converting lacZ to gfp reporter fusions in diverse bacteria," *Gene* 372:219-226 (2006); Scheffel, A. Schüller, D., "The Acidic Repetitive Domain of the *Magnetospirillum* gryphiswaldense MamJ Protein Displays Hypervariability but Is Not Required for Magnetosome Chain Assembly," *J Bacteriol.* 189(17):6437-6446 (2007); each publication incorporated herein by reference in its entirety for all purposes). The mating reactions were cultured for 10 days under defined microaerophilic conditions in the absence of DAP to select for positive transformants.

Following conjugation, gfp+AMB-1 transformants with and without the Shine-Dalgarno sequence successfully displayed GFP fluorescence. The transformants containing the Shine-Dalgarno sequence displayed higher levels of GFP fluorescence than the transformants without this sequence. The resulting fluorescence did not leave the gfp+AMB-1 cells when viewed at 100× magnification at 488 nm excitation.

The magnetic properties of the gfp+AMB-1 were analyzed by MM. The gfp+AMB-1 were suspended in agar plugs using a 1.5T instrument to optimize and characterize the imaging properties. FIG. 1 shows the positive contrast generated with a $T_1$ pulse sequence over a log scale concentration up to ~$10^8$ MTB/mL. Signal intensity was related to concentration.

B. Microinjection into Murine Embryonic Cells.

The gfp+AMB-1 were microinjected into one cell of each of 170 mouse embryos at the 2-cell stage. Six concentrations over a log scale up to ~$10^5$ gfp+AMB-1 were injected per cell, estimated by the optical density at 565 nm. Death rate of cells following microinjection was constant across the different injected concentrations. Images overlaying fluorescent and differential interference contrast (DIC) images of cells injected with the highest concentration ($10^5$ MTB/cell) were compared. An uninjected control exhibited low levels of autofluorescence. Slices at different horizontal planes in 8-cell embryos at a given time point were compared. In each embryo, all four cells derived from the injected cell showed significant fluorescence while none of the four cells derived from the uninjected internal controls displayed significant fluorescence.

Figures 2A, 2B:
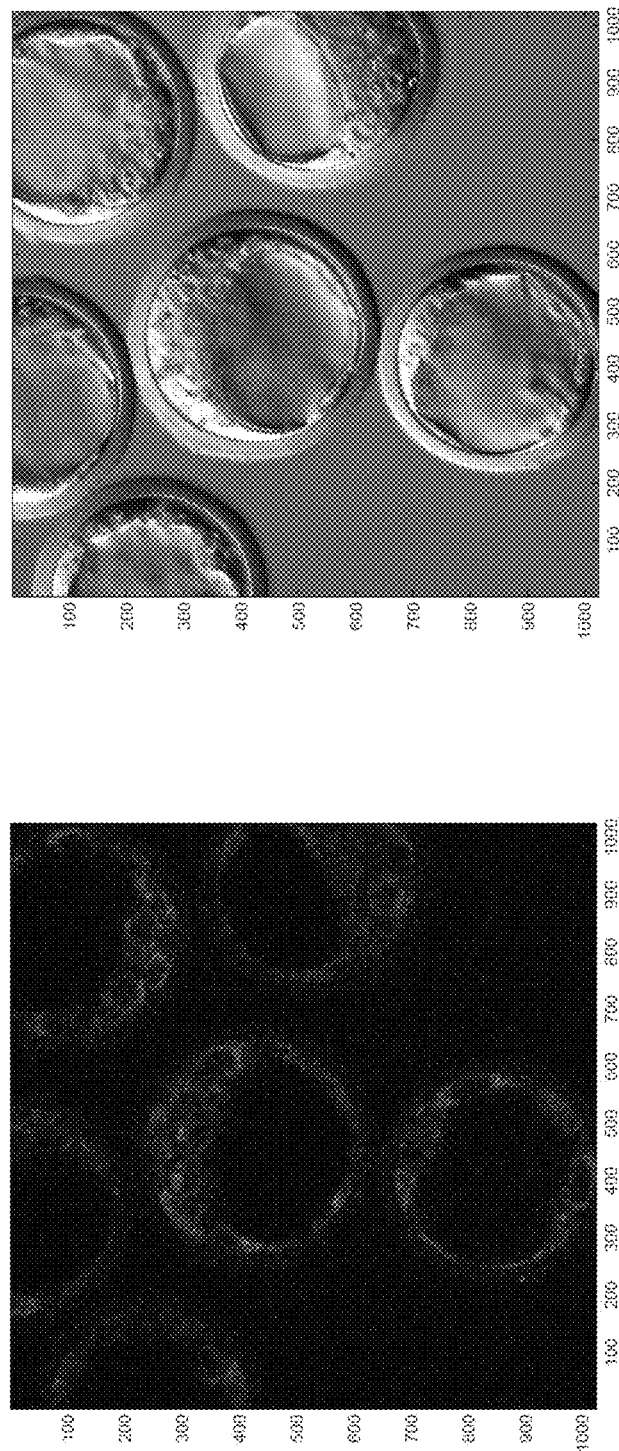
FIG. 2A-B shows a blastula stage mouse embryo that has had one of its two cells at the 2-cell embryo stage microinjected with gfp$^+$AMB-1. The embryo is imaged with Leica SP2 AOBS spectral confocal inverted microscope surrounded by an environmental control chamber for live-cell imaging with 20×, 0.7 NA objective, and optical zoom of 3×.

The embryos were allowed to develop for three days after the injection. In each concentration level, embryos survived for up to the full three days developing to the 256 cell blastula stage and appeared healthy enough for implantation. Numerous cells within each blastula displayed significant fluorescence, demonstrating that the artificial endosymbionts were transferred to daughter cells across multiple cell divisions as the embryos comprising the eukaryotic host cells developed to the blastula stage. One such blastula is shown in FIG. 2, where panel A shows a differential interference contrast (DIC) image of the blastula and panel B) shows a gray scale fluorescence capture of the same image, showing fluorescence in numerous cells throughout the blastula.

Figure 3:
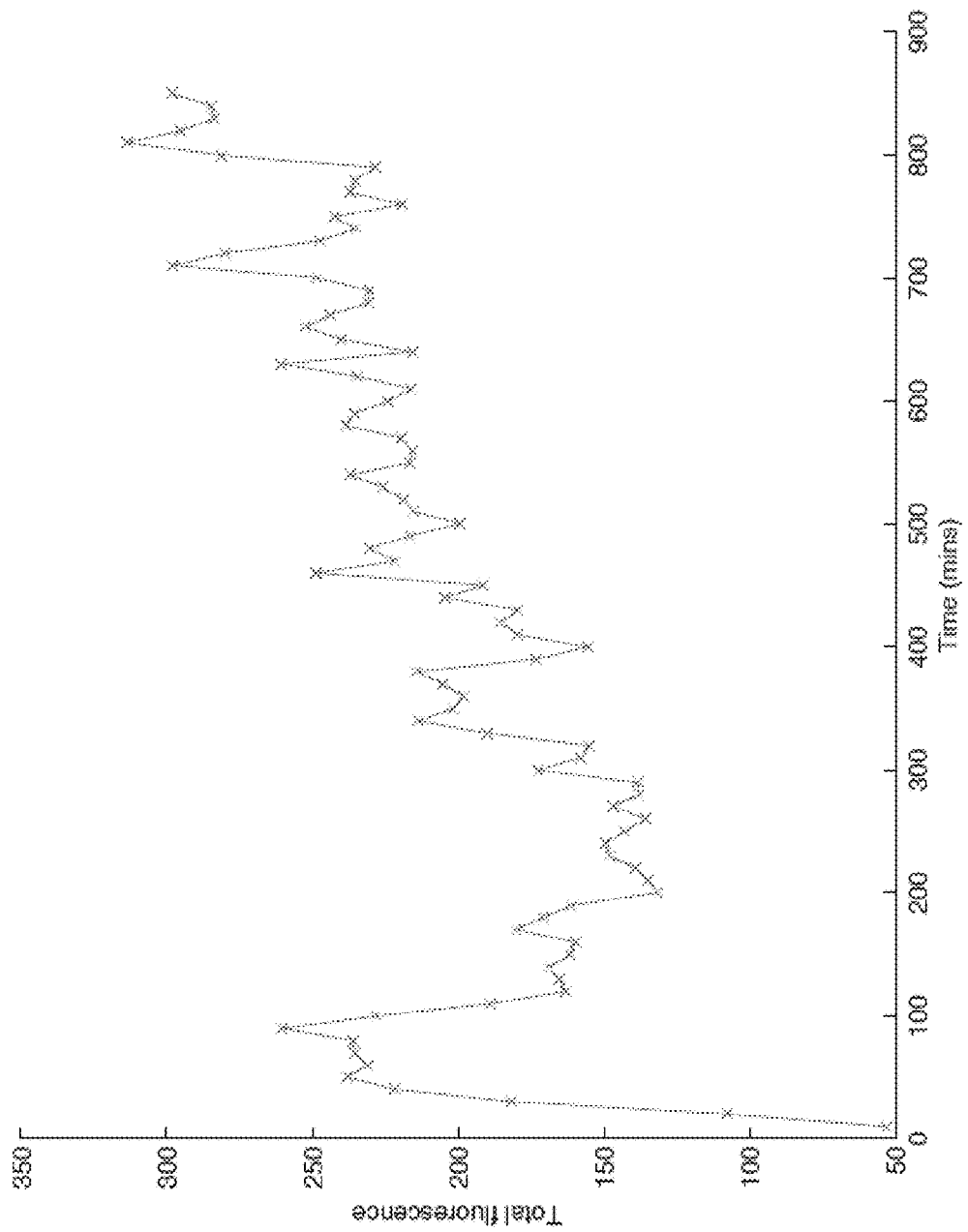
FIG. 3 shows the change of total embryo GFP fluorescence of four mouse embryos over time as measured by confocal microscopy. One of the two cells from the 2-cell stage of each embryo had been microinjected with gfp$^+$ AMB-1, and the total GFP fluorescence of each embryo was measured beginning at the 8-cell stage, 24 hours after microinjection.

Confocal microscopy was used to quantify total expression of GFP throughout four individual embryos by measuring total GFP fluorescence in the entire embryo over time at various points beginning at the eight cell stage of the embryo. FIG. 3 shows the change of embryo fluorescence over time. This indicates that the copy number of artificial endosymbionts was maintained in daughter cells for at least seven generations, such that the fluorescent phenotype of the host cells was maintained as the embryo progressed from the 2-cell stage to the 256-cell blastula stage.

These results demonstrate that, when delivered by microinjection, gfp+AMB-1 were not immediately cleared or degraded and were not toxic to the developing embryo over the course of the three day experiment. Microinjected embryos divided normally, suggesting that gfp+AMB-1 do not display pathogenic markers or secret toxic compounds. They were transferred to daughter cells across many cell divisions, were contained in the cytoplasm, were punctate and well distributed, and maintained copy number within the daughter host cells, such that the fluorescent phenotype of the eukaryote host cells was maintained in daughter cells through at least seven generations. These results demonstrate that AMB-1 can be stably maintained intracellularly and are transferred to daughter cells over at least seven cell divisions.

Example 2: Phagocytic Entry of AMB-1

Receptor mediated: The inlAB gene is amplified from *L. monocytogenes* genomic DNA (ATCC 19114) and is inserted into pBBR1MCS-5, the gentamicin cognate of pBBR1MCS-2 (see Kovach, M. E., et al., "Four new derivatives of the broad-host-range cloning vector pBBR1MCS, carrying different antibiotic-resistance cassettes," *Gene* 166, 175-176, (1995)), and gfp+inlAB+ AMB-1 is generated. The gfp+inlAB+ AMB-1 is co-cultured with eukaryotic host cells, including common epithelial tumor cell lines Coco-2, MDA-MB-231 and MCF7, non-epithelial tumor cell lines, such as HT-1080 and HL60, and murine stem cells. Fluorescent microscopy and FACS are used to monitor and quantify internalization and intracellular location.

Expression of pore-forming haemolysin (hlyA) in AMB-1 is achieved through amplification of hlyA from *L. monocytogenes* genomic DNA (ATCC 19114). The amplified hlyA is inserted into pBBR1MCS-3 (the tetracycline cognate of pBBR1MCS-2), which is then used to transform gfp+AMB-1. The resulting AMB-1 strain is exposed to murine macrophage cell line J774, capable of spontaneous phagocytosis. Gentomycin treatment is used to eliminate bacteria not internalized and hlyA⁻AMB-1 is used as negative control. Fluorescent microscopy is used to monitor the intracellular fate and localization of AMB-1.

If bacteria remain confined to the phagosomes, two genes, plcA and plcB, implicated in escape of *L. monocytogenes* into the cytosol, are introduced. (Smith, G. A. et al., *Infection and immunity* 63:4231 (1995); Camilli, A. et al., *J Exp Med.* 173:751 (1991); each publication incorporated herein by reference in its entirety for all purposes). If bacteria escape successfully, but fail to propagate, hpt is introduced (see Goetz, M. et al., *Proc Natl Acad Sci USA* 98:12221 (2001); Chico-Calero, I. et al., *Proc Natl Acad Sci USA* 99:431 (2002); each publication incorporated herein by reference in its entirety for all purposes). In *L. monocytogenes*, hpt encodes the transporter responsible for uptake of glucose-6-phosphate from the cytosol. Other genes from *L. monocytogenes* have been implicated in sustaining growth within host (glnA and gltAB and argD) and these are systematically introduced as needed. (Joseph, B. et al., *J Bacteriol.* 188:556 (2006), incorporated herein by reference in its entirety for all purposes).

Example 3: Regulation of AMB-1 Growth

Regulation of AMB-1 growth in embryonic stem cells can be regulated as follows. Coleoptericin-A (ColA) is amplified from total *Sitophilus oryzae* cDNA. Expression of ColA in beetles of genus *Sitophilus* regulates titers of γ-Protobacterium, which has naturally developed close symbiotic relationship the beetles, and resides in specific cells called bacteriocytes. (Login, F. H. et al., "Antimicrobial peptides keep insect endosymbionts under control," *Science* 334 (6054):362-365 (2011), incorporated herein by reference in its entirety for all purposes).

Murine embryonic stem cells comprising gfp+AMB-1 are treated using a neural differentiation protocol. MTB expression levels are quantified using qPCR and fluorescent microscopy. Amplified colA is then expressed in the gfp+

AMB-1 embryonic stem cells. A promoter is selected to provide optimal ColA expression levels.

Example 4: Magnetic Phenotype of Murine Cells Containing Gfp+AMB-1

Cells from macrophage cell line J774.2 derived from murine ascites and solid tumor with introduced gfp+AMB-1 were applied to a magnetic column and were retained by the column. These results demonstrate that, following introduction of gfp+AMB-1, J774.2 murine cells were magnetically detected and magnetically manipulated, as they were magnetically concentrated and magnetically collected.

Example 5: Gfp+AMB-1 in Human Breast Cancer Cell Line MDA-MB-231

Gfp+AMB-1, Gfp+InlA/B+AMB-1, and Gfp+Pla1+AMB-1 were each introduced to human breast cancer cells from cell line MDA-MB-231. GFP fluorescence was detected in more than 90% of the MDA-MB-231 cells 48 hours after the introduction of each of Gfp+AMB-1, Gfp+InlA/B+AMB-1, and Gfp+Pla1+AMB-1. GFP fluorescence in Gfp+AMB-1 was observed in these MDA-MB-231 cells at least 13 days after introduction of gfp+AMB-1, in the fourth passage of the MDA-MB-231 cells following the introduction, where MDA-MB-231 cell population doubled three to four times between each passage. GFP fluorescence was observed in both forming daughter cells of an MDA-MB-231 cell with introduced gfp+AMB-1 in the process of cell division.

Following the introduction of gfp+AMB-1, MDA-MB-231 cells were stained with Lysotracker® Red DND-99 dye (specific to lysosomes) and Hoechst 33342 nuclear stain purchased from Life Technologies. Green GFP fluorescence was observed as localized within individual MDA-MB-231 cells and distinct from red lysosome staining and blue nuclear staining suggesting that AMB-1 were localized in cytoplasm and not digested through lysosome pathway.

At 24 hours and 72 hours after introduction, plated MDA-MB-231 cells and plated control MDA-MB-231 cells were fixed in formalin and glutaraldehyde following a wash with PBS. Cells were then stained with Prussian Blue, and observed by microscopy at 40× magnification. Iron staining was observed in some of the MDA-MB-231 cells with introduced gfp+AMB-1 but not in the control MDA-MB-231 cells without introduced gfp+AMB-1. The proportion of cells displaying iron staining was similar between the MDA-MB-231 cells 72 hours after gfp+AMB-1 introduction and the MDA-MB-231 cells 24 hours after gfp+AMB-1 introduction.

48 hours after the introduction of gfp+AMB-1, MDA-MB-231 cells were trypsinized and resuspended in PBS. One sample of these cells was placed into a glass slide chamber. A magnet was aligned to the side of chamber and cell movement was observed under microscope at 20× magnification. MDA-MB-231 cells with introduced gfp+AMB-1, but not control MDA-MB-231 cells which had not had gfp+AMB-1 introduced, exhibited movement toward the magnet. Another sample of these cells was placed into small tubes, which were taped to a magnet for one hour. Control MDA-MB-231 cells which had not had gfp+AMB-1 introduced settled down at the bottom of the tube. However, MDA-MB-231 cells with introduced gfp+AMB-1 were aligned to the magnet side of the tubes.

These results indicate that gfp+AMB-1 were not immediately cleared from human breast cancer MDA-MB-231 cells. They were transferred to daughter cells across at least 12 cell divisions and were located within the MDA-MB-231 cells outside of both the lysosomes and nuclei. These results also demonstrate that at least 48 hours following introduction of gfp+AMB-1, the MDA-MB-231 cells containing gfp+AMB-1 displayed were magnetically detected and magnetically manipulated, as they were magnetically moved, magnetically targeted to a location, magnetically concentrated, and magnetically collected. Additionally, at least 72 hours following introduction of gfp+AMB-1, the MDA-MB-231 cells contained observable quantities of iron.

Example 6: Gfp+AMB-1 in Human Induced Pluripotent Stem Cells

GFP fluorescence was observed in Human Induced Pluripotent Stem ("IPS") cells at least eight days following introduction of gfp+AMB-1 to the IPS cells, in the second passage of the IPS cells. These results indicate that gfp+AMB-1 were not immediately cleared from human IPS cells, and were transferred to daughter cells.

Example 7: Cell Imaging within Mouse Tumor

Cell visualization was tested in a mouse bearing two subcutaneous tumors, one on its left flank and one on its right flank. $1.5 \times 10^6$ MDA-MB-231 cells containing introduced gfp+AMB-1 were injected directly into the tumor on the left flank of the mouse. An equivalent number of control MDA-MB-231 cells without introduced cells were injected on the right flank of the mouse. The mouse was imaged using a bench top 1T MM with T2w pulse sequences. The resulting image showed a dark area at the tumor on the right side of the mouse, the site of the injection of MDA-MB-231 cells containing introduced gfp+AMB-1, but no signal at the tumor on the right side of the mouse, where control MDA-MB-231 cells injected into a left side tumor.

Example 8: Monitoring of Mouse Tumor

Gfp+AMB-1 cells are introduced into MDA-MB-231 human cancer cells. The resulting magnetic cells and their daughter cells are injected into mammary fat pads of a group of immunocompromised mice. Tumor growth is monitored at regular intervals by MM imaging. Mice with established tumors assigned either to an experimental group or to a control group. Mice in the experimental group are treated with a potential anti-tumor therapeutic compound while mice in the control group are treated with an inactive vehicle. MM is used to monitor the size and growth of the tumor non-invasively following the treatments to assess the efficacy of the tested compound in combating the tumor.

Example 9: Magnetic Enhancement of Cell Retention

Gfp+AMB-1 cells are introduced into Rat Cardiac-Derived Stem Cells (CDC). The resulting magnetic CDC cells are used in the Ischemia/Reperfusion model. Rats are treated as described in Cheng K. et al., "Magnetic enhancement of cell retention, engraftment, and functional benefit after intracoronary delivery of cardiac-derived stem cells in a rat model of ischemia/reperfusion," *Cell Transplant.* 21(6): 1121-35 (2012). The magnetic CDC cells are then introduced into the left ventricle cavity of the treated rates. A 1.3 T magnet is placed above the heart during and after the injection. The animal's chest is closed and it is allowed to recover. The short and long-term behavior of the labeled CDC in the rat is monitored by MM imaging at regular intervals.

Example 10: AMF Tumor Treatment

Gfp+AMB-1 cells are introduced into MDA-MB-231 cells. The resulting cells are injected into subcutaneous tumors, formed by 4T1 cells in nude mice. Untreated control MDA-MB-231 cells are injected into a tumor at the opposite flank of each animal. Each animal is placed into alternating magnetic field (30.6 kA/m, 118 kHz) for 30 minutes, and allowed to recover following the procedure. Animals are sacrificed at regular intervals and histological analyzes are performed on tumors from both mice with injected magnetic MDA-MB-231 and control mice with injected control MDA-MB-231. In the experimental mice, the labeled cells and the surrounding tumor are damaged leading to damage to the tumor overtime.

Example 11: Bioluminescent AMB-1

Gene sequences of *Photorhabdus luminescens* luxCD-ABE operon were PCR amplified from pXen-13 plasmid (Perkin Elmer Hopkinton, Mass.) and cloned into pBBR1-MCS2 by using In-Fusion® HD Cloning Kit (Clontech, Mountain View, Calif., USA). Positive clones were confirmed by showing right size insert by restriction digest analysis and luminescence detection by a luminescence reader. Purified plasmids were introduced to mating strain *E. coli* WM3064. AMB-1 and WM3064 strains were mated for plasmid transfer and kanamycin resistant AMB-1 strains were selected. Luminescence positive strains were cultured in liquid MG medium. Luminescence was confirmed for lux+ AMB-1 alone using a benchtop luminometer. Magnetic properties were confirmed using CMag measurements. Strains were introduced into eukaryotic cells through either co-centrifugation or incubation with a strong magnet next to the cell container. Magnetic properties were confirmed by MRI phantoms and also by observing magnetic sensitivity in a microscope or by being trapped on a magnetic column.

Example 12: Creation of Fluorescent AMB-1

In an embodiment, genetically modified magnetotactic bacteria detectable by FLI are made using enhanced Green Fluorescent Protein (eGFP) inserted into the suicide plasmid pJQ200 and introduced into a diaminopimelic acid auxotrophic *E. coli* strain, which was used for mating with AMB-1. Gentamicin resistant strains were selected and fluorescence was confirmed by fluorescent microscopy. After 3 passages in gentamicin media, the cells were grown for a further 3 passages without antibiotic selection. They were then grown in the presence of 1% sucrose for 6 days and plated for single colonies on MGB agar plates. Single colonies were checked for GFP. Detection was performed using a Nikon Ti-S inverted epifluorescence microscope, using a FITC filter and a 40× objective. Fluorescent spiral-shaped bacteria can be observed at 40× magnification.

GFP-positive AMB-1 were inserted into MDA-MB-231, 4T1, hAMSC, J774.2, MCF-7 (and other) cells. gfp+ AMB-1 labeled and unlabeled cells were observed using a fluorescence microscope, and a clear enhancement in cellular fluorescence was observed with the gfp+ AMB-1 labeled cells, often with a punctate pattern that suggests localization in intracellular vesicles.

Figure 6A:
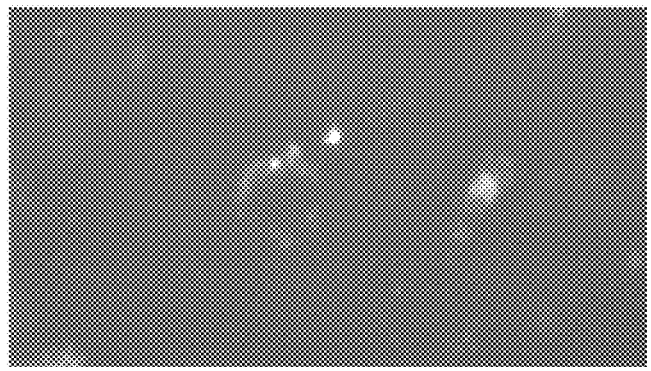
FIGS. 6A-L show different cells without gfp+ AMB-1 compared to cells containing gfp+ AMB-1. Cells are imaged with an epifluorescence microscope and fluorescence imaging. iPS (induced pluripotent stem cells, FIGS. 6A and 6B), MDA-MB-231 (breast carcinoma cells, FIGS. 6C and 6D), J774.2 cells (murine macrophage, FIGS. 6E and 6F), BJ (human fibroblast, FIGS. 6G and 6H), HEP1 cells (human liver adenocarcinoma, FIGS. 6I and 6J), and MCF7 (human epithelial breast adenocarcinoma, FIGS. 6K and 6L) were used.
Figure 6B:
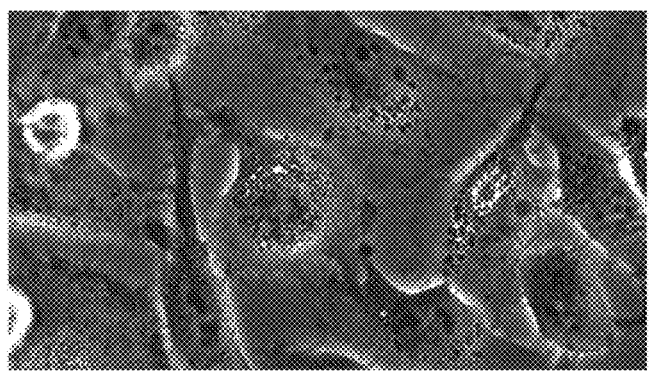
Figure 6C:
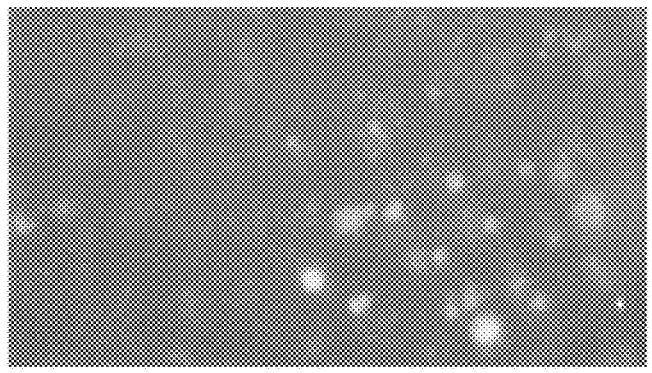
Figure 6D:
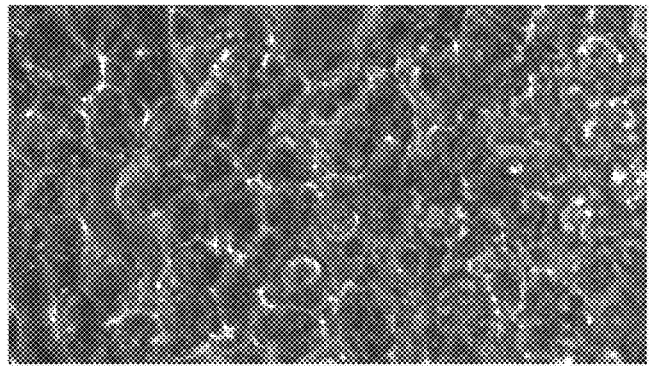
Figure 6H:
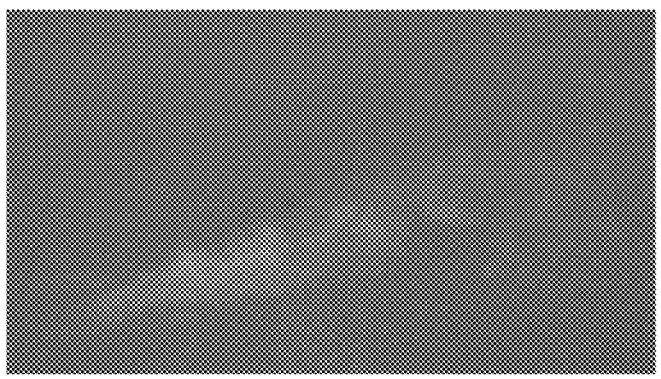
Figure 6G:
Figure 6F:
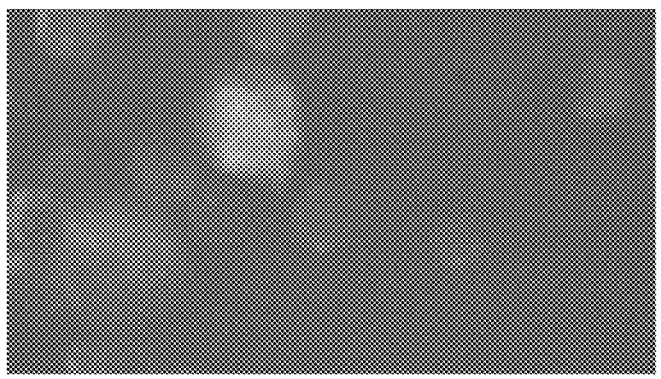
Figure 6E:
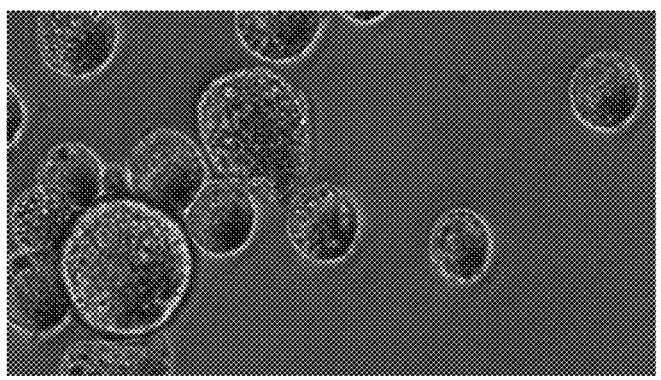
Figure 6L:
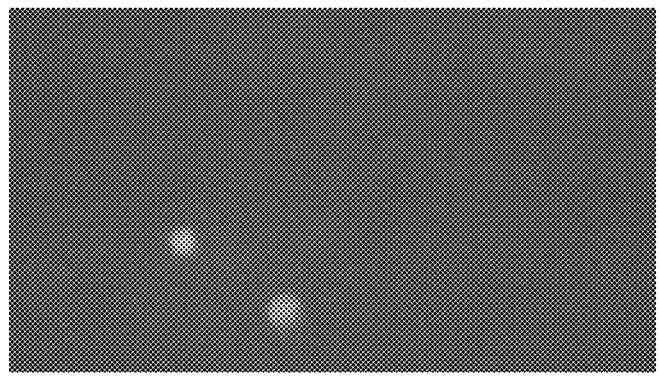
Figure 6K:
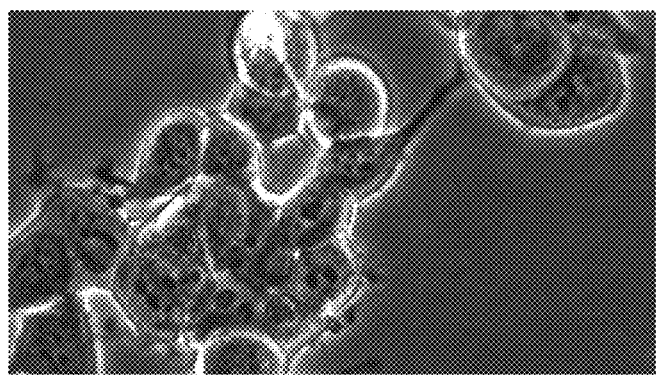
Figure 6J:
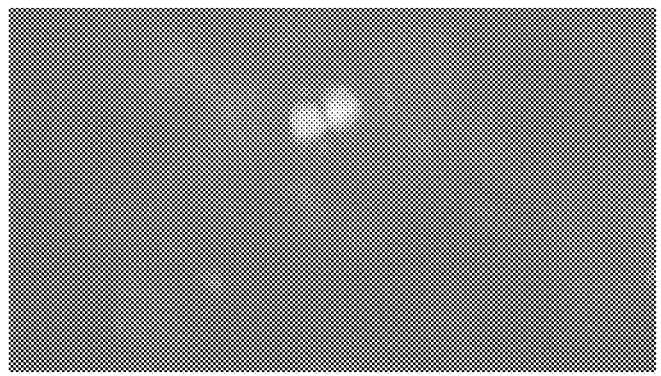
Figure 6I:

FIGS. 6A-L shows confocal microscopy and fluorescence images of the iPS cells (pluripotent stem cells) containing gfp+ AMB-1, MDA-MB-231 cells (human breast carcinoma) containing gfp+ AMB-1, J774.2 cells (murine macrophages) containing gfp+ AMB-1, BJ cells (human fibroblasts) containing gfp+ AMB-1, HEP1 cells (human liver adenocarcinoma) containing gfp+ AMB-1, and MCF-7 cells (human epithelial breast adenocarcinoma) containing gfp+ AMB-1. gfp+ AMB-1 were inserted into these cell lines and microscopy images were acquired using a Nikon Ti-S epi-fluorescence microscope with phase contrast optics or a FITC fluorescence filter, with a 40× magnification lens. FIGS. 6A-B show phase contrast and fluorescence images of iPS cells (pluripotent stem cells) containing gfp+ AMB-1. FIGS. 6C-D show phase contrast and fluorescence images of MDA-MB-231 cells (human breast carcinoma) containing gfp+ AMB-1. FIGS. 6E-F show phase contrast and fluorescence images of J774.2 cells (murine macrophages) containing gfp+ AMB-1. FIGS. 6G-H show phase contrast and fluorescence images of BJ cells (human fibroblasts) containing gfp+ AMB-1. FIGS. 6I-J show phase contrast and fluorescence images of HEP1 cells (human liver adenocarcinoma) containing gfp+ AMB-1. FIGS. 6K-L show phase contrast and fluorescence images of MCF-7 cells (human epithelial breast adenocarcinoma) containing gfp+ AMB-1. All these cell types showed enhanced fluorescence when the cells contained gfp+ AMB-1.

Example 13: Creation of PET Detectable AMB-1

To create PET-enabled genetically modified magnetotactic bacteria, the gene sequence for human simplex virus thymidine kinase (HSV1-Tk) can be introduced via an appropriate plasmid containing a selection gene (e.g. for kanamycin or gentamicin antibiotic resistance) into WM3064, which can subsequently be mated with AMB-1 for plasmid transfer. Antibiotic-resistant AMB-1 strains can then be selected. Positive expression of the reporter can be evaluated by adding the radiolabelled HSV1-Tk substrate 3H-PCV (penciclovir), and quantifying AMB-1 uptake using a scintillation counter.

PET reporter-positive AMB-1 can be inserted into MDA-MB-231, 4T1, hAMSC, J774.2, MCF-7 (and other) cells. AMB-1 labeled and unlabeled cells can be injected into a living subject, and then the subject would be injected with a radiolabelled substrate for the HSV1-TK reporter gene (e.g. $^{18}$F-FHBG). After 1 hour, a PET scan of the subject would show a pronounced uptake in the region of the AMB-1 labeled cells.

Example 14: Detection of Eukaryotic Cells Containing AMB-1 with Fluorescence Imaging and MRI MDA-MB-231 cells containing gfp+ AMB-1 were grown to confluence. MDA-MB-231 cells containing gfp+ AMB-1 and MDA-MB-231 cells without gfp+ AMB-1 were imaged with confocal microscopy and fluorescence imaging. Phase contrast and fluorescence images were acquired using a Nikon Ti-S epi-fluorescence microscope with phase contrast optics or a FITC fluorescence filter, with a 40× magnification lens. Fluorescence images were exposed for 0.5 seconds. FIGS. 4A and 4D show phase contrast images of MDA-MB-231 with and without gfp+ AMB-1. FIGS. 4B and 4E show fluorescence imaging of MDA-MB-231 with and without gfp+ AMB-1. FIG. 4B demonstrates the fluorescent signal from the gfp+ AMB-1 in the MDA-MB-231 cells.

MDA-MB-231 cells with and without gfp+ AMB-1 were prepared for imaging with MM as follows. MDA-MB-231 cells with and without gfp+ AMB-1 were trypsinized and 2 million cells were resuspended in 100 μl PBS. Cell suspensions were pipetted into PCR tubes containing pre-solidified 100 μl 1% agarose. PCR tubes were sealed and left for 10 minutes to allow cells to settle on the agarose/PBS boundary. A Varian 7T 300 MHz Horizontal Bore preclinical MR system was used. The scanner featured a 40 G/cm 120 mm High Duty Cycle Gradient Coil. Images were acquired with vnmrj 4.0 image acquisition software. Phantom tubes were imaged using a 2D T2w MEMS sequence (TR 3000 ms, TE Min 7 ms, NE 48, NEX 1, 128×128, 40×40 mm FOV, 1 mm slice thickness, coronal view, tubes were imaged using a Rapid F19 volume coil. MRI images are shown in FIGS. 4C (MDA-MB-231 with gfp+ AMB-1) and 4F (MDA-MB-231 without gfp+ AMB-1). A dark band is seen in FIG. 4C identifying the location of the MDA-MB-231 with gfp+ AMB-1. No such dark band is seen in FIG. 4F.

Figure 5C:
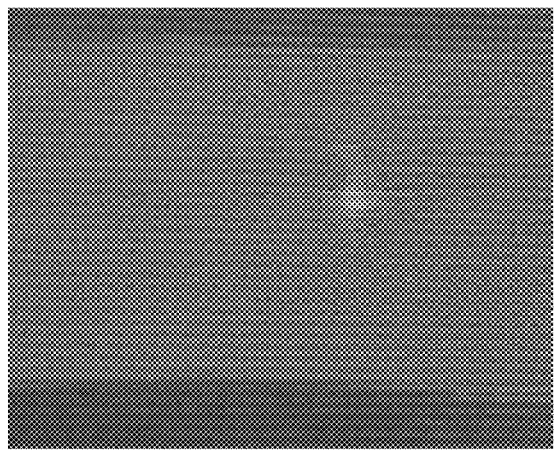
FIGS. 5A-C show MDA-MB-231 cells containing gfp+ AMB-1, suspended in agarose gel in a cylindrical 100 ml tube.
Figure 5B:
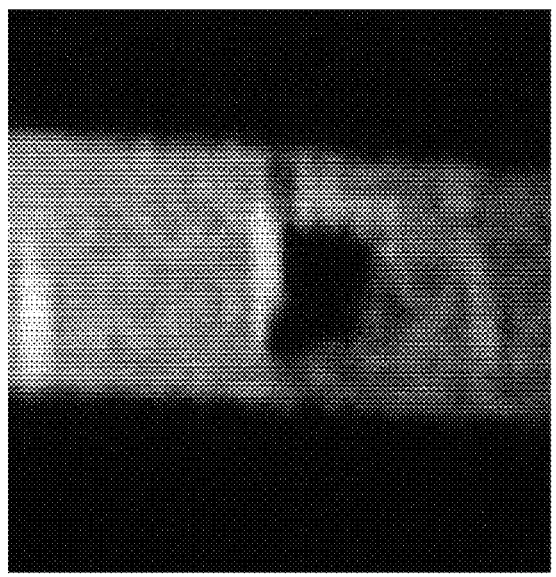
Figure 5A:
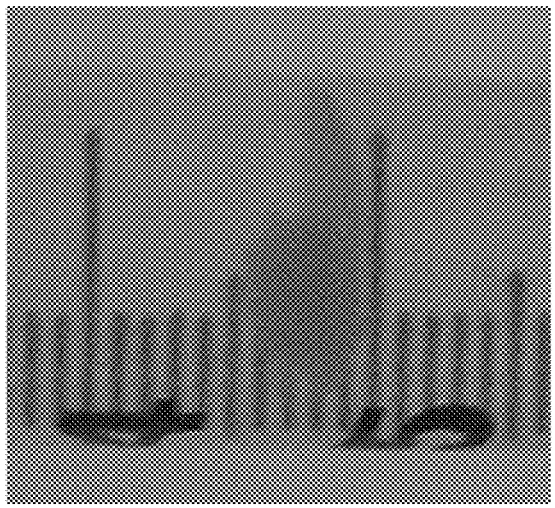

FIGS. 5A-C shows a lower magnification example of MRI, fluorescence, and visual inspection imaging of MDA-MB-231 cells with gfp+ AMB-1. MDA-MB-231 cells were labeled with gfp+ AMB-1, washed after 24 hours, trypsinized and harvested at 48 hours, spun down in a centrifuge, and the resultant pellet was suspended in 1% agarose gel in a cylindrical 100 cc tube. Fluorescence images were obtained on an IVIS 49 fluorescence imager, using a Cy5.5 filter and a 1 second acquisition time. An MRI image was obtained on a Bruker ICON 1T preclinical MRI scanner, with a T2w RARE pulse sequence (TR 1500 ms, TE 96 ms, FA 180 degrees, acquisition time 5 mins, FOV 3.5 cm, 128×128, slice thickness 1.25 mm, interslice gap 1.00 mm), with a 2.5 cm diameter rat coil. FIGS. 5A-C show different modality detection of the same MDA-MB-231 cells with gfp+ AMB-1 suspended in agarose. FIG. 5A shows the MDA-MB-231 cells viewed by visual inspection of the plastic tube. FIG. 5B shows an MRI image of the MDA-MB-231 cells with gfp+ AMB-1 in the same tube. FIG. 5C shows a fluorescence image of the MDA-MB-231 cells in the same tube. The MDA-MB-231 cells with gfp+ AMB-1 are detectable using MRI and fluorescence imaging.

Example 15: Detection of AMB-1 with Luminescence and MRI

Figure 7B:
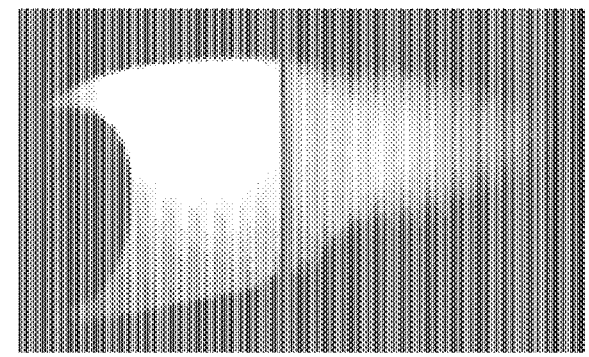
FIGS. 7A-B show MDA-MB-231 cells containing lux+ AMB-1 imaged for luminescence or imaged with MM.
Figure 7A:
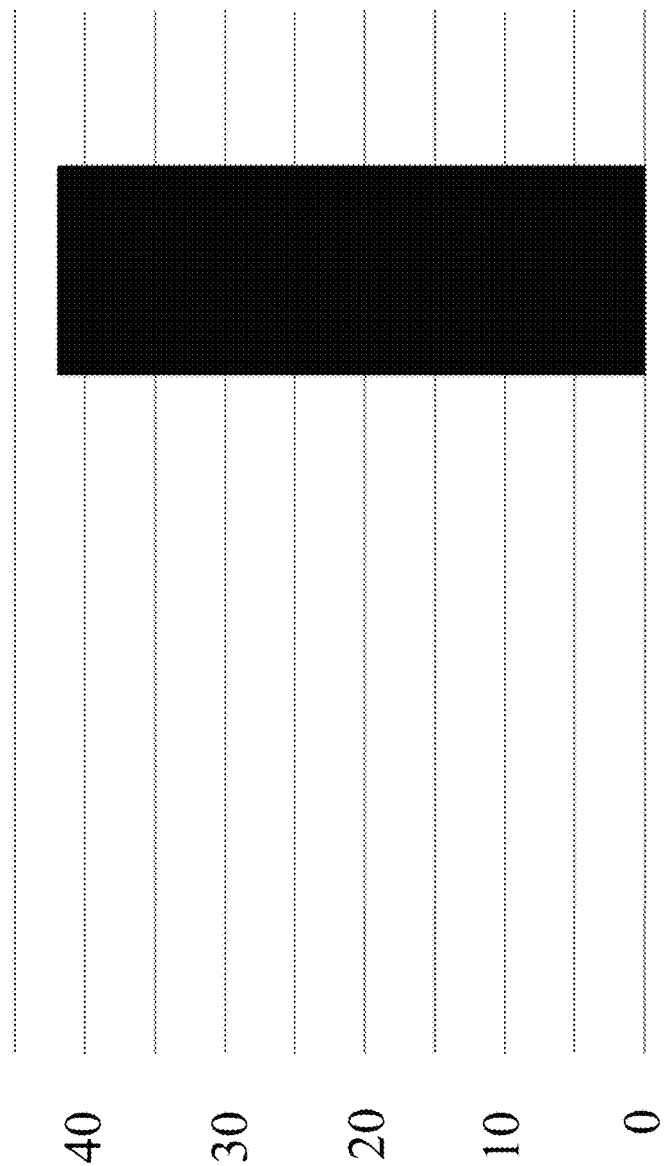

AMB-1 was transfected with a pBBR1-MCS2 lux plasmid to make luminescent AMB-1. These luminescent AMB-1 were introduced into MDA-MB-231 cells. MDA-MB-231 cells contain the lux+ AMB-1 were grown to confluence and 1 million cells subject to luminosity measurements on a TD-20/20 luminometer using the manufactures protocol. Measurements were obtained for 1 minute and results were standardized for OD400=1. FIG. 7A shows a chart comparing the luminescence signal from the MDA-MB-231 cells with luminescent AMB-1 to MDA-MB-231 cells without AMB-1. MDA-MB-231 cells with luminescent AMB-1 yielded a significant luminescence signal compared to MDA-MB-231 cells without AMB-1.

An MRI image of MDA-MB-231 cells with luminescent AMB-1 was obtained as follows. MDA-MB-231 cells with luminescent AMB-1 were trypsinized and 2 million cells were resuspended in 100 μl PBS. Cell suspensions were pipetted into PCR tubes containing pre-solidified 100 μl 1% agarose. PCR tubes were sealed and left for 10 minutes to allow cells to settle on the agarose/PBS boundary. Images were acquired on a Discovery MR901 preclinical 7T MRI, actively shielded; Bore diameter—310 mm, Gradients: (120 mm ID, 600 mT/m, 6000T/m/s), 8 Receive channels; 1 MHz at 16 bits per channel. A T2*w GRE sequence was used for imaging sample (TR 300 ms, TE 30 ms, NEX 2, 256×256, 30 mm FOV). FIG. 7B shows an MRI image of MDA-MB-231 cells with luminescent AMB-1. The MDA-MB-231 cells with luminescent AMB-1 are seen as a dark band in the middle of the tube.

All publications, patents and patent applications discussed and cited herein are incorporated herein by reference in their entireties. It is understood that the disclosed invention is not limited to the particular methodology, protocols and materials described as these can vary. It is also understood that the terminology used herein is for the purposes of describing particular embodiments only and is not intended to limit the scope of the present invention which will be limited only by the appended claims.

Those skilled in the art will recognize, or be able to ascertain using no more than routine experimentation, many equivalents to the specific embodiments of the invention described herein. Such equivalents are intended to be encompassed by the following claims.

We claim:

1. A method for detecting the location and viability of a eukaryotic cell, comprising the steps of: obtaining the eukaryotic cell, wherein the eukaryotic cell comprises a magnetic bacterium; and magnetically imaging the eukaryotic cell whereby the location and viability of the eukaryotic cell is determined.

2. The method of claim 1, wherein the eukaryotic cell is contained in a mammal.

3. The method of claim 2, wherein the mammal is a murine.

4. The method of claim 2, wherein the mammal is a human.

5. The method of claim 2 wherein the the magnetic imaging is performed with a magnetic resonance imaging, a magnetic particle imaging, or a magnetic relaxation switching imaging.

6. The method of claim 2, wherein the eukaryotic cell is a mesenchymal stem cell.

7. The method of claim 2, wherein the eukaryotic cell is a neural stem cell.

8. The method of claim 2, wherein the eukaryotic cell is an iPS cell.

9. The method of claim 2, wherein the eukaryotic cell is a T-cell.

10. The method of claim 2, wherein the eukaryotic cell is a cancer cell.

11. A method for detecting the location and viability of a stem cell, comprising the steps of: obtaining the stem cell, wherein the stem cell comprises a magnetic bacterium; magnetically imaging the stem cell whereby the location and viability of the stem cell is determined.

12. The method of claim 11, further comprising the step of activating the stem cell to proliferate.

13. The method of claim 11, further comprising the step of activating the stem cell to differentiate.

14. The method of claim 11, wherein the stem cell is contained in a mammal.

15. The method of claim 14, wherein the mammal is a mouse.

16. The method of claim 14, wherein the mammal is a human.

17. A method for detecting the location and viability of a neural progenitor cell, comprising the steps of: obtaining a neural progenitor cell, wherein the neural progenitor cell comprises a magnetic bacterium; magnetically imaging the neural progenitor cell whereby the location and viability of the neural progenitor cell is determined.

18. The method of claim 17, wherein the neural progenitor cell is contained in a mammal.

19. The method of claim 18, wherein the mammal is a human.

20. The method of claim 17, further comprising the step of proliferating the neural progenitor cell.

* * * * *